US007358041B2

(12) United States Patent
Short et al.

(10) Patent No.: US 7,358,041 B2
(45) Date of Patent: Apr. 15, 2008

(54) ANTIBODIES TO MAGMAS AND USES THEREOF

(76) Inventors: Mary K. Short, 50 Winter Park Dr., Hopewell Junction, NY (US) 12533; Paul T. Jubinsky, 50 Winter Park Dr., Hopewell Junction, NY (US) 12533

(*) Notice: Subject to any disclaimer, the term of this patent is extended or adjusted under 35 U.S.C. 154(b) by 0 days.

(21) Appl. No.: 10/498,458

(22) PCT Filed: Dec. 2, 2002

(86) PCT No.: PCT/US02/38325

§ 371 (c)(1), (2), (4) Date: Oct. 7, 2004

(87) PCT Pub. No.: WO03/048317

PCT Pub. Date: Jun. 12, 2003

(65) Prior Publication Data

US 2005/0089928 A1 Apr. 28, 2005

Related U.S. Application Data

(60) Provisional application No. 60/339,455, filed on Dec. 11, 2001, provisional application No. 60/334,365, filed on Nov. 30, 2001.

(51) Int. Cl.
*C12Q 1/00* (2006.01)
*G01N 33/53* (2006.01)
*C07K 14/435* (2006.01)

(52) U.S. Cl. ........................... 435/4; 435/7.1; 530/300

(58) Field of Classification Search .................... None
See application file for complete search history.

(56) References Cited

FOREIGN PATENT DOCUMENTS

| | | |
|---|---|---|
| WO | WO 00/05367 | 2/2000 |
| WO | WO 00/58473 | 10/2000 |
| WO | WO 00/71581 | 11/2000 |

*Primary Examiner*—Ruixiang Li
(74) *Attorney, Agent, or Firm*—Nixon Peabody LLP

(57) ABSTRACT

The present invention relates to isolated and purified Magmas protein, isolated and purified nucleic acids encoding Magmas protein, and antibodies to Magmas protein, which interacts with granulocyte macrophage colony stimulating factor (GM-CSF). More specifically, the invention relates to uses of such anti-Magmas antibodies. The invention further relates to a method for diagnosis, prognosis and treatment of diseases, particularly, cancer, Alzheimer's disease and mitochondrial diseases using Magmas sequences and antibodies directed against the Magmas protein or fragments thereof.

3 Claims, 9 Drawing Sheets

```
Human:   1                                                    ggagtttgagcccc  14
Mouse:   1 CTGACCCACCAGCAACCCTTGAGCTGGTCCCACTGGGTCGGGAAGCGGCACCCGTCCCCc  60

Human:  15 ggaggcagagcggctgccatggccaagtacctggcccagatcattgtgatgggcgtgcag  74
Mouse:  61 taaagtggagcgtccgccatggccaagtacctggcccagatcattgtgatgggtgtgcag 120
                                M  A  K  Y  L  A  Q  I  I  V  M  G  V  Q

Human:  75 gtggtgggcagggcctttgcacgggccttgcggcaggagtttgcagccagccgggccgca 134
Mouse: 121 gtggtgggcagagcctttgccagggccctgaggcaggagtttgcagccagccaggcagcc 180
           V  V  G  R  A  F  A  R  A  L  R  Q  E  F  A  A  S  Q  A  A

Human: 135 gctgatgcccgaggacgcgctggacaccggtctgcagccgcttccaacctctccggcctc 194
Mouse: 181 gctgacgctcgagggcgtgctgggcaccagtctgcagctgcatccaatctctctggcctc 240
           A  D  A  R  G  R  A  G  H  Q  S  A  A  A  S  N  L  S  G  L

Human: 195 agcctccaggaggcacagcagattctcaacgtgtccaagctgagccctgaggaggtccag 254
Mouse: 241 agcctccaggaagcccagcagattctcaacgtctccaagctgagccccgaggaggtccag 300
           S  L  Q  E  A  Q  Q  I  L  N  V  S  K  L  S  P  E  E  V  Q

Human: 275 aagaactatgaacacttatttaaggtgaatgataaatccgtgggtggctccttctacctg 314
Mouse: 301 aagaattatgaacacctatttaaagtgaatgataagtccgtgggtggctctttctacctg 360
           K  N  Y  E  H  L  F  K  V  N  D  K  S  V  G  G  S  F  Y  L

Human: 315 cagtcaaaggaggtccgaacaaaggagcgcctggatgaggaactcaaaatccaggcccag 374
Mouse: 361 cagtcaaaggttgtccgtgcaaaggaacgtctagatgaggaactccgaatacaagcccag 420
           Q  S  K  V  V  R  A  K  E  R  L  D  E  E  L  R  I  Q  A  Q

Human: 375 gaggacagagaaaaagggcagatgccccatacgtgactgctcggctccccccgcccaccc 434
Mouse: 421 gaagacagagagaaagggcagaagcccaaaacgtgactgctgggctCTCCACACCCCAGc 480
           E  D  R  E  K  G  Q  K  P  K  T  *

Human: 435 cgccgcctc.taatttatagcttggtaataaa...........tttcttttctgc      477
Mouse: 481 CATTGCctcataatttatagcctagtaataaatgtctttgcgtgtttcttcactgc      536
```

*FIG. 3A*

ANTIBODIES TO MAGMAS AND USES THEREOF

CROSS-REFERENCE TO RELATED APPLICATIONS

This application is a 371 National Phase Entry Application of co-pending International Application PCT/US02/38325, filed 2 Dec. 2002, which designated the U.S. and which claims the benefit under 35 U.S.C. § 119(e) of U.S. Provisional Application 60/334,365, filed 30 Nov. 2001 and U.S. Provisional Application 60/339,455, filed 11 Dec. 2001.

FIELD OF INVENTION

The present invention relates to isolated and purified Magmas protein, isolated and purified nucleic acids encoding Magmas protein, and antibodies to Magmas protein, which interacts with granulocyte macrophage colony stimulating factor (GM-CSF). More specifically, the invention relates to uses of such anti-Magmas antibodies. The invention further relates to a method for diagnosis, prognosis and treatment of diseases using Magmas sequences and antibodies directed against the Magmas protein.

BACKGROUND OF THE INVENTION

GM-CSF and interleukin 3 (IL-3) are two of many growth factors that affect the survival, growth and differentiation of hematopoietic cells. The receptors for these factors consist of an a subunit that is responsible for the specificity of ligand binding and a shared subunit known as the common β chain (βc). The significant α subunit homology together with shared β subunit composition of these receptor complexes accounts for the similar activities that IL-3 and GM-CSF have on hematopoietic cells.

The signal transduction pathways of IL-3 and GM-CSF are nearly identical [1]. An early event for both following ligand binding is the tyrosine phosphorylation of βc which is believed to be important in the activation of several signal transduction pathways. Jak2 which is constitutively bound to βc in the absence of growth factor is one of the kinases responsible for the tyrosine phosphorylation of βc [2]. Phosphorylated tyrosine residues on βc allow interactions with proteins containing src homology 2 domains (SH2) such as Shc [3, 4 ], Shp-2 [5], and STAT 5 [6]. Activated Jak2 also phosphorylates bound STAT 5 molecules resulting in homo- or heterodimerization with other STATs and entry into the nucleus where they act as transcriptional regulators of a variety of genes [7]. Shc interactions with βc leads to recruitment of grb2 and sos[8], and activation of Ras [9] and MAP kinase. GM-CSF and IL-3 activation of PI3K [10, 11] also appears to be mediated through βC via interactions with lyn [12, 13], and possibly SHP2 [14]. RACK1 is another molecule which is constitutively bound to βC in the absence of ligand [15]. This protein may regulate the activities of the tyrosine kinases Src and Lck and protein kinase C. However survival and at least a limited degree of proliferation has been shown to occur in cells with a mutant βC that does not contain any tyrosine residues, demonstrating redundancy in the signaling process [16, 17].

Growth factors are essential for the survival, proliferation and differentiation of normal and malignant cells. GM-CSF, along with IL-6, EGF, and IGF-1 are among the growth factors known to be important regulators of carcinoma cells, e.g., prostate carcinoma cells [45] [72][73][74][76][47][63].

For example, the GM-CSF receptor is expressed in prostate carcinoma cell lines and in primary prostate tumor[47][63]. Some prostate carcinomas even produce GM-CSF, which results in autocrine mediated proliferation and growth factor independence [75][77]. Identifying key regulatory proteins and pathways involved in GM-CSF signaling would be useful for the development of new modalities for the detection and treatment of cancer, e.g. prostate cancer.

Cancer of the prostate is the most commonly diagnosed cancer in men and is the second most common cause of cancer death (Carter, et al., 1990; Armbruster, et al., 1993). If detected at an early stage, prostate cancer is potentially curable. However, a majority of cases are diagnosed at later stages when metastasis of the primary tumor has already occurred (Wang, et al., 1982). Early diagnosis is problematic because the current tests tend to provide a substantial number of false positives and many individuals who test positive in these screens do not develop cancer. Present treatment for prostate cancer includes radical prostatectomy, radiation therapy, or hormonal therapy. No systemic therapy has clearly improved survival in cases of hormone refractory disease. With surgical intervention, complete eradication of the tumor is not always achieved and the observed reoccurrence of the cancer (12-68%) is dependent upon the initial clinical tumor stage (Zietman, et al., 1993). Thus, alternative methods of diagnosis, and treatment including prognosis, prophylaxis or prevention woudl desirable.

Mitochondria are cellular organelles with various tasks, including cellular energy production. Therefore, mitochondrial disorders most commonly manifest in tissues highly dependent on biological energy: the brain, heart, muscle and the main sense organs, in particular the eye and inner ear. Mitochondrial diseases include phenotypes resembling several rather common conditions, such as myopathy, hearing impairment, epilepsy, diabetes, muscle weakness or paralysis.

Mitochondrial disorders can be caused by mutations in the genes in mitochondrial DNA (mtDNA) or nuclear DNA. While mtDNA encodes only 37 genes, the number of nuclear DNA genes that encode proteins essential for mitochondrial function is unknown. Identification of these novel nuclear genes would be an important step in diagnostic and prognostic analysis and eventually treatment of mitochondrial diseases associated with defects in the proteins encoded by the nuclear genes.

Alzheimer's Disease ("AD") is a neurodegenerative illness characterized by memory loss and other cognitive deficits. McKhann et al., Neurology 34: 939 (1984). It is the most common cause of dementia in the United States. AD can strike persons as young as 40-50 years of age, yet, because the presence of the disease is difficult to determine without dangerous brain biopsy, the time of onset is unknown. The prevalence of AD increases with age, with estimates of the affected population reaching as high as 40-50% by ages 85-90. Evans et al., JAMA 262: 2551 (1989); Katzman, Neurology 43: 13 (1993).

By definition, AD is definitively diagnosed through examination of brain tissue, usually at autopsy. Khachaturian, Arch. Neurol. 42: 1097 (1985); McKhann et al., Neurology 34: 939 (1984). Neuropathologically, this disease is characterized by the presence of neuritic plaques (NP), neurofibrillary tangles (NFT), and neuronal loss, along with a variety of other findings. Mann, Mech. Ageing Dev. 31: 213 (1985).

Thus far, diagnosis of AD has been achieved mostly through clinical criteria evaluation, brain biopsies and post mortem tissue studies. Research efforts to develop methods for diagnosing Alzheimer's disease in vivo include (1) genetic testing, (2) immunoassay methods and (3) imaging techniques.

SUMMARY OF THE INVENTION

The present invention is directed to antibodies to a newly identified protein encoded by nuclear DNA, and uses of such antibodies. The invention further provides the nucleic acid and amino acid sequence of Magmas and variations of the nucleic acid and amino acid sequence of the Magmas providing useful diagnostic tools for cancer. The invention is based upon our discovery, purification and isolation of a novel mitochondrial and ribosome associated protein, Magmas, that has a role in GM-CSF activity that differs from IL-3 and without wishing to be bound by a theory, it also potentially interacts with other signal transduction pathways.

The antibodies of the present invention are useful, for example, in detecting variations of Magmas expression levels. Variations of the expression level of Magmas appear to be associated with a number of disease states including, mitochondrial myopathy, Alzheimer's disease and cancer, particularly prostate cancer, neuroblastoma, Ewings sarcoma, osteosarcoma and leukemia, particularly acute myeloid leukemia (AML) and acute lymphoid leukemia (ALL). We have also discovered that the Magmas is associated with ribosomal subunits, particularly with ribosomal subunit S19. Therefore, antibodies to Magmas are also useful in methods of diagnosing diseases related to ribosomal dysfunction such as, Diamond Blackfan anemia We have also discovered a method for diagnostic and prognostic analysis of any of the above mentioned diseases using these Magmas antibodies. We have further discovered a method of treating such cancers using the antibodies directed against the Magmas protein. Additionally, we have identified assays that can be used to screen for novel compounds that can interact with Magmas. We have also identified a method of diagnosing and treating mitochondrial disorders associated with Magmas. Additionally, the novel Magmas sequence variations of the present invention provide diagnostic tool for AML, ALL as well as mitochondrial myopathy.

In one embodiment, the invention provides an isolated and purified nucleic acid sequence comprising SEQ ID NO: 11 or fragments thereof that consist of preferably at least 20, 30, 50, 100, or 500 contiguous nucleic acids of the SEQ ID NO: 11. Nucleic acids encoding a protein having at least 85%, preferably at least 90%, more preferably at least 95%, 98%, or 99% homology to SEQ ID NO: 4 are also provided. Homology as used herein is determined using a NCBI BLAST nucleotide homology comparison program, or "BLAST" using its default settings.

In another embodiment, the invention provides an isolated and purified nucleic acid sequence encoding SEQ ID NO: 4 or fragments thereof that consist of preferably at least 6, 8, 10, 20, or 50 contiguous amino acids of SEQ ID NO: 4.

Preferably, the fragments are selected from the group consisting of amino acids 1-29, 1-32, 1-33, 30-125, 33-125, 34-125, of SEQ ID NO: 4. These sequences are useful, for example, in preparing antibodies to diagnose cancers which are associated with Magmas mutations resulting in deletions in Magmas protein as described below. Vectors comprising the nucleic acid sequences and fragments thereof are also provided.

The invention further provides isolated and purified nucleic acid sequences encoding amino acid sequences of the SEQ ID NO: 5, SEQ ID NO: 6; SEQ ID NO: 7; SEQ ID NO: 8; SEQ ID NO: 9 and vectors comprising such sequences.

In another embodiment, the invention provides an isolated and purified protein comprising SEQ ID NO: 4 or a fragment thereof having at least 6 contiguous amino acids of SEQ ID NO: 4 or an amino acid sequence having at least 85%, more preferably at least 90% and most preferably at least 95%, 98% or 99% homology to SEQ ID NO: 4 as defined using the BLAST with the standard settings.

The invention further provides nucleic acids encoding fusion proteins comprising SEQ ID NO: 4 or a fragment thereof.

In one embodiment, the invention relates to an antibody or antibody fragment directed against an immunogenic fragment of a Magmas protein. As used herein, the term "Magmas protein" refers to a protein having the amino acid sequence of the SEQ ID NO: 4.

In another embodiment, the invention relates to a complex comprising an antibody or antibody fragment directed against an immunogenic fragment of a Magmas protein linked to a cytotoxic molecule.

In another embodiment, the invention relates to a complex comprising an antibody or antibody fragment directed against an immunogenic fragment of a Magmas protein linked to a detectable label. In one embodiment, the detectable label is a radionuclide.

In yet another embodiment, the invention entails a method of detecting cancer comprising the steps of providing a biological sample from an individual suspected of having cancer, analyzing the Magmas protein expression in the sample, comparing the expression of Magmas protein in the sample against a normal control, wherein increased expression of the Magmas protein in the sample indicates that the individual is at increased risk for cancer. The expression of the Magmas protein can be analyzed using either Magmas mRNA or Magmas protein. In the preferred embodiment the analysis is an immunohistochemical analysis with an antibody directed against Magmas protein. Preferably the cancer is prostate cancer, neuroblastoma, Ewings sarcoma, osteosarcoma and leukemia. Most preferably, the cancer is prostate cancer.

In another embodiment, the invention entails a method of determining the severity of the cancer comprising the steps of taking a biological sample of an individual suspected of having prostate cancer, analyzing the Magmas protein expression in the sample, comparing the expression of the Magmas protein in the sample to a normal sample and/or comparing the expression of the Magmas protein in the sample to expression in a panel of samples comprising of tissue samples representing different stages of prostate cancer. The expression profile of the Magmas protein in the sample indicates the stage of prostate cancer and provides prognostic information and guidance that can be used, for example in designing treatment options.

In one embodiment, the invention provides a method of diagnosing Alzheimer's disease in an individual in vivo wherein an anti-Magmas antibody is coupled with a radionuclide and injected to an individual's brain wherein reduced labeling of the pyramidal neurons of the hippocampus indicate that the individual is affected with Alzheimer's disease. The individual is considered affected when the reduction in labeling with the anti-Magmas antibody is at least about 50-60% of the amount in a sample from a control individual, i.e. an individual not affected with Alzherimer's disease.

In yet another embodiment, the invention relates to a method of treating an individual affected with cancer comprising the steps of administering a therapeutic Magmas blocking amount of a compound that interacts with Magmas such as a Magmas antibody in a pharmaceutically acceptable carrier to an individual having prostate cancer.

In another embodiment, the invention relates to a method of treating an individual affected with prostate cancer comprising the steps of administering a therapeutic cancer treating amount of Magmas-antibody-cytotoxic molecule complex in a pharmaceutically acceptable carrier to an individual having prostate cancer.

In one embodiment, the invention relates to a method of diagnosing a mitochondrial disorder comprising the steps of providing a biological sample from an individual suspected of having a mitochondrial disorder, analyzing the Magmas protein expression in the sample, comparing the expression of Magmas protein in the sample against a normal control, wherein decreased expression of the Magmas protein or expression of a truncated protein or expression of a protein with a number of mutations in the sample indicates that the individual has a mitochondrial disorder. The expression of the Magmas protein can be analyzed using either Magmas mRNA or Magmas protein. In the preferred embodiment the analysis is an immunohistochemical analysis with an antibody directed against Magmas protein.

In another embodiment, the invention relates to a method of determining the severity of a mitochondrial associated disorder comprising the steps of taking a biological sample of an individual suspected of having a mitochondrial disease, analyzing the Magmas protein expression in the sample, comparing the level of expression of the Magmas protein or expression of a truncated protein or expression of a protein with a number of mutations in the sample to a normal sample and/or comparing the expression of the Magmas protein in the sample to expression in a panel of samples comprising of tissue samples representing different degrees of severity of a mitochondrial disorder. The expression profile of the Magmas protein in the sample indicates the stage of mitochondrial disorder and provides prognostic information and guidance that can be used, for example in designing treatment options.

The invention further provides a method of diagnosing mitochondrial myopathy by detecting the sequence variation E72G in the SEQ ID NO: 4 corresponding to a nucleic acid substitution A247G of SEQ ID NO: 11.

In one embodiment, the invention provides a method of diagnosing AML or ALL in an individual. The method comprises obtaining a biological sample, preferably a bone marrow sample, from an individual suspected of having AML or ALL and analyzing the size, sequence and/or presence of the Magmas protein in the sample.

In one embodiment, a sequence variation of Magmas located between nucleic acid A132 and G133 in the SEQ ID NO: 11 resulting in a deletion in the SEQ ID NO: 4 indicates that the individual is affected with AML or ALL. In another embodiment, a sequence variation of Magmas located between G141 and G142 of SEQ ID NO: 11 resulting in a deletion in the SEQ ID NO: 4 indicates that the individual is affected with AML or ALL. In yet another embodiment, the sequence variation located between G228 and A229 of SEQ ID NO: 11 resulting in a deletion in the SEQ ID NO: 4 indicates that the individual is affected with AML or ALL. The term "sequence variation" is meant to include all kinds of mutations including deletions, insertions, inventions and single nucleotide substitutions. Preferably the sequence variation results in a truncated Magmas protein.

In one embodiment, the analysis is performed using two antibodies. First antibody is directed to an antigenic fragment, preferably the N-terminal part, of Magmas protein which is present in both a normal and mutant Magmas protein, and the second antibody is directed to an epitope which is not present in the mutant Magmas. A tissue sample is labeled with the first and the second antibody wherein reduced labeling using the second antibody indicates that the individual is affected with an AML or ALL. Preferably, the antibody against a C-terminal fragment of SEQ ID NO: 4 is the C-terminal fragment beginning at amino acid 29 of SEQ ID NO: 4 and the N-terminal antibody is an antibody against an N-terminal fragment of SEQ ID NO: 4 before the amino acid 29 of the SEQ ID NO: 4.

Alternatively, the analysis of the Magmas can be performed using DNA or RNA samples and analyzing the Magmas deletion mutations using, for example PCR-based methods, wherein the deleted sequences are detected, for example using primers flanking the deletion region and wherein amplification product using such primers results in a shorter than the normal Magmas fragment if the sample contains a deletion-mutant Magmas allele.

BRIEF DESCRIPTION OF FIGURES

FIGS. 3A and B show a cDNA alignment, sequence analysis, and protein structure of Magmas. FIG. 3A provides comparison of cDNA and protein sequence of human (nucleic acids beginning from nucleotide number 15 of SEQ ID NO: 11 are shown) and mouse Magmas (SEQ ID NO: 12). The amino acid single letter code is displayed below the mouse cDNA sequence. The five amino acids that differ between murine and human Magmas are in bold print (glutamine 32 to arginine; glutamine 44 to arginine; arginine 110 to lysine; lysine 122 to methionine; lysine 124 to histidine). Amino acids encoding the leader sequence are underlined.

FIG. 7A shows a Western blot of Magmas expression. Protein lysates from untransfected PGMD1 cells or cells transfected with vectors containing sense or antisense Magmas cDNA were subjected to polyacrylamide gel electrophoresis and the proteins were transferred to nitrocellulose membranes. The membrane was blotted with rabbit polyclonal anti-Magmas antibody followed by peroxidase conjugated goat anti-rabbit antibody and chemilumenscence reagent.

DETAILED DESCRIPTION OF THE INVENTION

We have now identified a mitochondrial associated protein, Magmas, that has a role in GM-CSF activity that differs from IL-3. The level of this protein appears to be associated with cancer, particularly prostate cancer, neuroblastoma, Ewings sarcoma, osteosarcoma and leukemia The level of Magmas is also affected in patients with Alzheimer's disease. In addition, mutation in Magmas was identified in a patient with a mitochondrial disease. Moreover, we have generated and discovered antibodies against the novel Magmas protein. We have also discovered a method for diagnostic and prognostic analysis of cancer using these Magmas antibodies. Any of the above-mentioned cancers can be diagnosed by looking for elevated levels of Magmas. Preferably, the cancer in prostate cancer. We have further discovered a method of treating such cancers using the antibodies directed against the Magmas protein. Additionally, we have identified assays that can be used to screen for novel compounds that can interact with magmas. Furthermore, we have discovered a method of diagnostic and prognostic analysis of mitochondrial disorders and Alzheimer's disease.

In one embodiment, the invention relates to an anti-Magmas antibody which refers to an antibody or antibody fragment directed against an immunogenic fragment of a Magmas protein.

Terms "Magmas" and "Magmas protein" refer to an amino acid sequence of SEQ ID NO: 4:

```
                                       (SEQ ID NO: 4)
MAKYLAQIIVMGVQVVGRAFARALRQEFAASRAAADARGRAGHRSAAASN

LSGLSLQEAQQILNVSKLSPEEVQKNYEHLFKVNDKSVGGSFYLQSKVVR

AKERLDEELKIQAQEDREKWQMPHT.
```

Homologues of Magmas as described by the SEQ ID NO: 4 that are at least 85% homologous with the SEQ ID NO: 4 as determined using the NCBI BLAST sequence analysis suit are also provided.

Figure 3B:
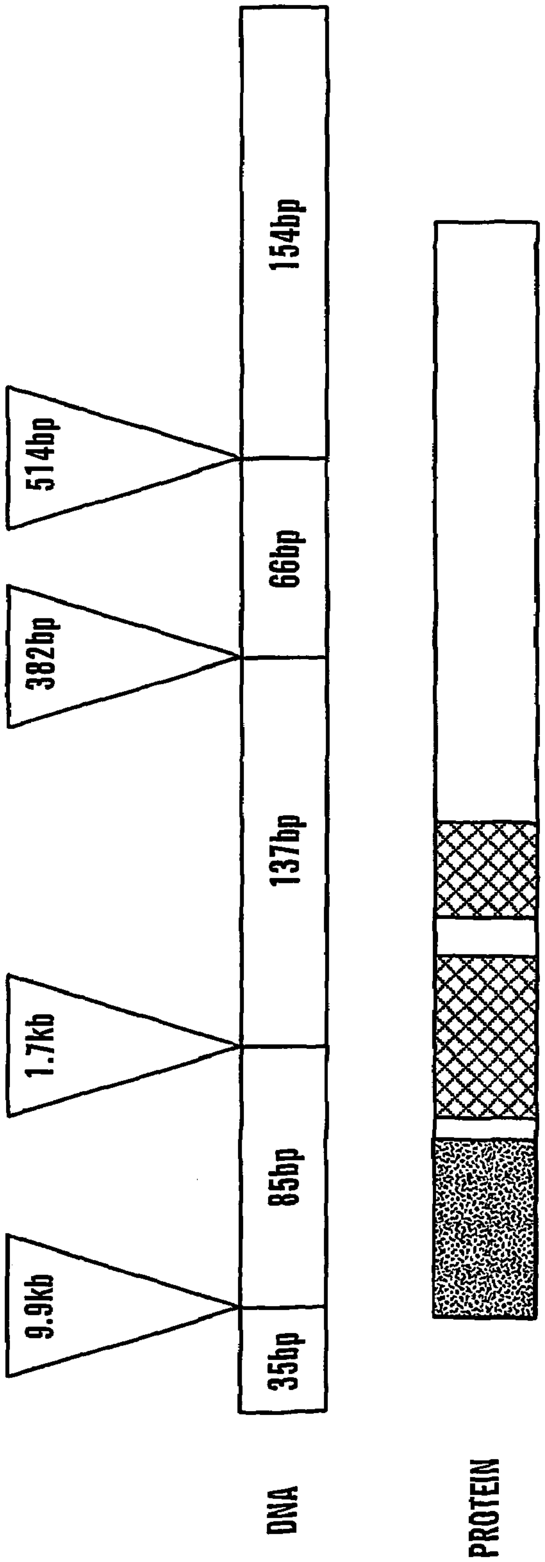
FIG. 3B is a schematic representation of the human genomic DNA (gDNA) organization and protein structure. The boundaries of exons are indicated by vertical lines with introns drawn as inverted triangles. Lengths are in kilobase (kb) or base pairs (bp). The corresponding Magmas protein schematic representation indicates the relative size and exon derivation of the 5' and 3' untranslated regions and coding regions. The leader sequence (black box), and areas of low compositional complexity (hatched boxes) are indicated.

FIG. 3B shows a schematic representation of the human genomic DNA (gDNA) organization and protein structure. The boundaries of exons are indicated by vertical lines with introns drawn as inverted triangles. Lengths are in kilobase (kb) or base pairs (bp). The corresponding Magmas protein schematic representation indicates the relative size and exon derivation of the 5' and 3' untranslated regions and coding regions. The leader sequence (black box), and areas of low compositional complexity (hatched boxes) are indicated.

The nucleic acid encoding the human Magmas, which allows one skilled in the art to design, for example, PCR primers, is depicted in the SEQ ID NO: 11 below.

```
  1 aattcggcac caggggagtt tgagccccgg agcagagcgg ctgccatggc caagtacctg  (SEQ ID NO: 11)

 61 gcccagatca ttgtgatggg cgtgcaggtg gtgggcaggg cctttgcacg ggccttgcgg

121 caggagtttg cagccagccg ggccgcagct gatgcccgag gacgcgctgg acaccggtct

181 gcagccgctt ccaacctctc cggcctcagc ctccaggagg cacagcagat tctcaacgtg

241 tccaagctga gccctgagga ggtccagaag aactatgaac acttatttaa ggtgaatgat

301 aaatccgtgg gtggctcctt ctacctgcag tcaaaggtgg tccgcgcaaa ggagcgcctg

361 gatgaggaac tcaaaatcca ggcccaggag gacagagaaa aatggcagat gccccatacg

421 tgactgctcg gctccccccg cccaccccgc cgcctctaat ttatagcttg gtaataaatt

481 tcttttctgc aaaaaa.
```

The term "Magmas antigen epitope" as used herein refers to a molecule which is capable of immunoreactivity with the anti-Magmas monoclonal antibodies of this invention. Magmas antigen epitopes may comprise proteins, protein fragments, peptides, carbohydrates, lipids, and other molecules, but for the purposes of the present invention are most commonly proteins, short oligopeptides, oligopeptide mimics (i.e., organic compounds which mimic the antibody binding properties of the Magmas antigen), or combinations thereof. Suitable oligopeptide mimics are described, for example, in PCT application US91/04282.

Particularly diagnostically useful epitopes include, for example, antibodies directed against the following peptide fragments region deleted in the following sequences (SEQ ID NOs: 5-9) as compared to the SEQ ID NO: 4 and antibodies against the peptides of SEQ ID NOs: 5-9:

```
                                        (SEQ ID NO: 5)
MAKYLAQIIVMGVQVVGRVFARALRQEFAFARALRQEFAELZ;

                                        (SEQ ID NO: 6)
MAKYLAQIIVMGVQVVGRAFARALRQEFAASRFQPLRPQPPGGTADSQRV
QAEPZ;

                                        (SEQ ID NO: 7)
MAKYLAQIIVMGVQVVGRAFARALRQEFAASRRHSRFSTCPSZ);

                                        (SEQ ID NO: 8)
MAKYLAQIIVMGVQVVGRAFARALRQEFAASTPZ

                                        (SEQ ID NO: 9)
MAKYLAQIIVMGVQVVGRAFARALRQEFAASRAEADARGRAGHRSAAASNL
SGLSLQEAQQKNYEHLFKVNDKSVGGSFYLQTKVVRAKERLDEELKIQAQ
EDRKKGQMPHTZ.
```

Antibodies can be prepared by means well known in the art. The term "antibodies" is meant to include monoclonal antibodies, polyclonal antibodies and antibodies prepared by recombinant nucleic acid techniques that are selectively reactive with a desired antigen such as Magmas protein or an antigenic epitope thereof.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized antibodies" means that at least a portion of the framework regions of an immunoglobulin are derived from human immunoglobulin sequences.

As used herein, the term "single chain antibodies" refer to antibodies prepared by determining the binding domains (both heavy and light chains) of a binding antibody, and supplying a linking moiety which permits preservation of the binding function. This forms, in essence, a radically abbreviated antibody, having only that part of the variable domain necessary for binding to the antigen. Determination and construction of single chain antibodies are described in U.S. Pat. No. 4,946,778 to Ladner et al.

The term "selectively reactive" refers to those antibodies that react with one or more antigenic determinants of the desired antigen, e.g., Magmas protein, and do not react appreciably with other polypeptides. For example, in a competitive binding assay, less than 5% of the antibody would bind another protein, preferably less than 3%, still more preferably less than 2% and most preferably less than 1%. Antigenic determinants usually consist of chemically active surface groupings ot molecules such as amino acids or sugar side chains and have specific three dimensional structural characteristics as well as specific charge characteristics. Antibodies can be used for diagnostic applications or for research purposes.

For example, antibodies may be raised against amino-terminal (N-terminal) or carboxyl-terminal (C-terminal) peptides of a Magmas polypeptide. Preferably 10-20 N-terminal or 10-25 C-terminal fragments of the Magmas protein are used.

One method of generating such an antibody is by using hybridoma mRNA or splenic mRNA as a template for PCR amplification of such genes [Huse, et al., *Science* 246:1276 (1989)]. For example, antibodies can be derived from murine monoclonal hybridomas [Richardson J. H., et al., *Proc Natl Acad Sci USA* Vol. 92:3137-3141 (1995); Biocca S., et al., *Biochem and Biophys Res Comm,* 197:422-427 (1993) Mhashilkar, A. M., et al., *EMBO J.* 14:1542-1551 (1995)]. These hybridomas provide a reliable source of well-characterized reagents for the construction of antibodies and are particularly useful when their epitope reactivity and affinity has been previously characterized. Another source for such construction includes the use of human monoclonal antibody producing cell lines. [Marasco, W. A., et al., *Proc Natl Acad Sci USA,* 90:7889-7893 (1993); Chen, S. Y., et al., *Proc Natl Acad Sci USA* 91:5932-5936 (1994)]. Another example includes the use of antibody phage display technology to construct new antibodies against different epitopes on a target molecule. [Burton, D. R., et al., *Proc Natl Acad Sci USA* 88:10134-10137 (1991); Hoogenboom H. R., et al., *Immunol Rev* 130:41-68 (1992); Winter G., et al., *Annu Rev Immunol* 12:433-455 (1994); Marks, J. D., et al., *J Biol Chem* 267: 16007-16010 (1992); Nissim, A., et al., *EMBO J* 13:692-698 (1994); Vaughan T. J., et al., *Nature Bio* 14:309-314 (1996); Marks C., et al., *New Eng J Med* 335:730-733 (1996)]. For example, very large naive human sFv libraries have been and can be created to offer a large source or rearranged antibody genes against a fragment of Magmas proteins.

Other sources include transgenic mice that contain a human immunoglobulin locus instead of the corresponding mouse locus as well as stable hybridomas that secrete human antigen-specific antibodies. [Lonberg, N., et al., *Nature* 368:856-859 (1994); Green, L. L., et al., *Nat Genet* 7:13-21 (1994)]. Such transgenic animals provide another source of human antibody genes through either conventional hybridoma technology or in combination with phage display technology. In vitro procedures to manipulate the affinity and fine specificity of the antigen binding site have been reported including repertoire cloning [Clackson, T., et al., *Nature* 352:624-628 (1991); Marks, J. D., et al., *J Mol Biol* 222:581-597 (1991); Griffiths, A. D., et al., *EMBO J* 12:725-734 (1993)], in vitro affinity maturation [Marks, J. D., et al., *Biotech* 10:779-783 (1992); Gram H., et al., *Proc Natl Acad Sci USA* 89:3576-3580 (1992)], semi-synthetic libraries [Hoogenboom, H. R., supra; Barbas, C. F., supra; Akamatsu, Y., et al., *J Immunol* 151:4631-4659 (1993)] and guided selection [Jespers, L. S., et al., *Bio Tech* 12:899-903 (1994)]. Starting materials for these recombinant DNA based strategies include RNA from mouse spleens [Clackson, T., supra] and human peripheral blood lymphocytes [Portolano, S., et al., supra; Barbas, C. F., et al., supra; Marks, J. D., et al., supra; Barbas, C. F., et al., *Proc Natl Acad Sci USA* 88: 7978-7982 (1991)].

Thus, one can readily screen an antibody to insure that it has a sufficient binding affinity for the Magmas protein or a fragment thereof. The binding affinity ($K_d$) should be at least about $10^{-7}$ l/mol, more preferably at least about $10^{-8}$ l/mol.

For example, cDNA clone in a vector, which are well known to one skilled in the art, encoding Magmas or a fragment thereof may be expressed in a host using standard techniques such that 5-20% of the total protein that can be recovered from the host is the desired protein. Recovered proteins can be electrophoresed using PAGE and the appropriate protein band can be cut out of the gel. The desired protein sample can then be eluted from the gel slice and prepared for immunization. Alternatively, a protein of interest can be purified by using conventional methods such as, for example, affinity chromatography, and molecular sizing, and ionic strength separation chromatographic procedures.

Once the protein immunogen is prepared, mice can be immunized twice intraperitoneally with approximately 50 micrograms of Magmas protein or a fragment thereof per mouse. Sera from such immunized mice can be tested for Magmas antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active Magmas antibodies according to the invention can be sacrificed three days later and their spleens removed for fusion and hybridoma production. Positive supernatants of such hybridomas can be identified using the assays described above and by, for example, Western blot analysis.

To further improve the likelihood of producing a Magmas specific antibody, the amino acid sequence of the polypeptide encoded by a eukaryotic nucleotide sequence of Magmas protein may be analyzed in order to identify portions of amino acid sequence which may be associated with increased immunogenicity. For example, polypeptide sequences may be subjected to computer analysis to identify potentially immunogenic surface epitopes. Such computer analysis can include generating plots of antigenic index, hydrophilicity, structural features such as amphophilic helices or amphophilic sheets and the like.

For preparation of monoclonal antibodies directed toward polypeptides encoded by a Magmas sequence of the invention, any technique that provides for the production of antibody molecules by continuous cell lines may be used. For example, the hybridoma technique originally developed by Kohler and Milstein (Nature, 256: 495-497, 1973), as well as the trioma technique, the human B-cell hybridoma technique (Kozbor et al., Immunology Today, 4:72), and the EBV-hybridoma technique to produce human monoclonal antibodies, and the like, are within the scope of the present invention. See, generally Larrick et al., U.S. Pat. No. 5,001,065 and references cited therein. Further, single-chain antibody (SCA) methods are also available to produce antibodies against polypeptides encoded by a eukaryotic nucleotide sequence of the invention (Ladner et al. U.S. Pat. Nos. 4,704,694 and 4,976,778).

Another method for preparing anti-Magmas antibodies is by in vitro immunization techniques, such as using spleen cells, e.g., a culture of murine spleen cells, injecting an antigen, and then screening for an antibody produced to said antigen. With this method, as little as 0.1 micrograms of Magmas antigen can be used, although about 1 microgram/milliliter is preferred. For in vitro immunization, spleen cells are harvested, for example, mice spleen cells, and incubated at the desired amount, for example, $1\times10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27-33 (1986)], Salmonella typhimurium mitogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841-845 (1984); Borrebaeck, C. A. K., *J. Immunol.* 136:3710-3715 (1986)] or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore Corp. The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find anti-Magmas antibodies of interest. Cultures containing the anti-Magmas antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186-187 (1993)].

This latter technique requires less antigen than the in vivo immunization because the in vivo method typically requires about 50 micrograms of antigen per mouse per injection and there are usually two boosts following primary immunization for the in vivo method.

Using any of these antibodies, one can construct $V_H$ and $V_L$ genes. For instance, one can create $V_H$ and $V_L$ libraries from murine spleen cells that have been immunized either by the above-described in vitro immunization technique or by conventional in vivo immunization and from hybridoma cell lines that have already been produced or are commercially available. One can also use commercially available $V_H$ and $V_L$ libraries. One method involves using the spleen cells to obtain mRNA which is used to synthesize cDNA. Double stranded cDNA can be made by using PCR to amplify the variable region with a degenative N terminal V region primer and a J region primer or with $V_H$ family specific primers, e.g., mouse-12, human-7.

For example, the genes of the $V_H$ and $V_L$ domains of the desired antibody, such as one to Magmas, can be cloned and sequenced. The first strand cDNA can be synthesized from, for example, total RNA by using oligo dT priming and the Moloney murine leukemia virus reverse transcriptase according to known procedures. This first strand cDNA is then used to perform PCR reactions. One would use typical PCR conditions, for example, 25 to 30 cycles using e.g. Vent polymerase to amplify the cDNA of the immunoglobulin genes. DNA sequence analysis is then performed. [Sanger, et al., *Proc. Natl. Acad Sci. USA* 79:5463-5467 (1977)].

Both heavy chain primer pairs and light chain primer pairs can be produced by this methodology. One preferably inserts convenient restriction sites into the primers to make cloning easier.

Thereafter, the variable region is chosen. This is then added to the "humanized" framework motif by standard techniques.

Those of ordinary skill in the art will recognize that a large variety of possible moieties can be coupled to the resultant anti-Magmas antibodies of the invention. See, for example, "Conjugate Vaccines", Contributions to Microbiology and Immunology, J. M. Cruse and R. E. Lewis, Jr (eds), Carger Press, New York, (1989), the entire contents of which are incorporated herein by reference.

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the anti-Magmas antibodies of the present invention, to other molecules. For example, representative coupling agents can include organic compounds such as thioesters, carbodiimides, succinimide esters, diisocyanates, glutaraldehydes, diazobenzenes and hexamethylene diamines. This listing is not intended to be exhaustive of the various classes of coupling agents known in the art but, rather, is exemplary of the more common coupling agents. (See, e.g. Killen and Lindstrom 1984, "Specific killing of lymphocytes that cause experimental Autoimmune Myasthenia Gravis by toxin-acetylcholine receptor conjugates." Jour. Immun. 133:1335-2549; Jansen, F. K., H. E. Blythman, D. Carriere, P. Casella, O. Gros, P. Gros, J. C. Laurent, F. Paolucci, B. Pau, P. Poncelet, G. Richer, H. Vidal, and G. A. Voisin. 1982. "Immunotoxins: Hybrid molecules combining high specificity and potent cytotoxicity". Immunological Reviews 62:185-216; and Ghetie and Vitetta, Chemical construction of immunotoxins. Mol Biotechnol. 2001 July;18(3):251-68.).

Preferred linkers are described in the literature. See, for example, Ramakrishnan, S. et al., Cancer Res. 44:201-208 (1984) describing use of MBS (M-maleimidobenzoyl-N-hydroxysuccinimide ester). See also, Umemoto et al. U.S. Pat. No. 5,030,719, describing use of halogenated acetyl hydrazide derivative coupled to an antibody by way of an oligopeptide linker. Particularly preferred linkers include: (i) EDC (1-ethyl-3-(3-diinethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6[3-(2-pyridyldithio)propionamido]hexanoate (Pierce Chem. Co., Cat #21651 G); (iv) Sulfo-LC-SPDP (sulfosuccinimidyl 6[3-(2-pyridyldithio)-propianamide]hexanoate (Pierce Chem. Co. Cat. #2165-G); and (v) sulfo-NHS (N-hydroxysulfosuccinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In another embodiment, the invention relates to a complex comprising an antibody or antibody fragment directed against an immunogenic fragment of a Magmas protein linked to a cytotoxic molecule. Various immunoconjugates in which antibodies were used to target chemotherapeutic drugs (P. N. Kularni, A. H. Blair, T. I. Ghose, Cancer Res. 41, 2700 (1981); R. Arnon, R. and M. Sela, Immunol. Rev. 62, 5 (1982); H. M. Yang and R. A. Resifeld, Proc. Natl. Acad. Sci. U.S.A., 85, 1189 (1988); R. O. Dilman, D. E. Johnson, D. L. Shawler, J. A. Koziol, Cancer Res. 48, 6097 (1988); L. B. Shih, R. M. Sharkey, F. J. Primus, D. M. Goldenberg, Int. J. Cancer 41, 832 (1988); P. A. Trail, et al., Cancer Res. 52, 5693 (1992)), or plant and bacterial toxins (I. Pastan, M. C. Willingham, D. J. Fitzgerald, Cell 47, 641 (1986); D. D. Blakey, E. J. Wawrzynezak, P. M. Wallace, P. E. Thorpe, in Monoclonal Antibody Therapy Prog. Allergy, H. Waldmann, Ed. (Karger, Basel, 1988), pp. 50-90) have been evaluated in preclinical models and found to be active in vitro and in vivo. A U.S. Pat. No. 5,869,045 describes in detail how to make such antibody conjugates and is hereby incorporated as reference in its entirety.

Examples of therapeutic agents that can be conjugated with anti-Magmas antibodies include, but are not limited to, antimetabolites, alkylating agents, anthracyclines, and antimitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunoribicin (formerly daunomycin) and doxorubicin (also referred to herein as adriamycin). Additional examples include mitozantrone and bisantrene. Antimitotic agents include vincristine and vinblastine (which are commonly referred to as vinca alkaloids). Other cytotoxic agents include procarbazine, hydroxyurea, asparaginase, corticosteroids, mytotane (O,P'-(DDD)), and interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid. Clearly analogs and homologs of such therapeutic and cytotoxic agents are encompassed by the present invention. For example, the chemotherapuetic agent aminopterin has a correlative improved analog namely methotrexate.

Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

Anti-Magmas antibodies of the present invention can be detected by appropriate assays, e.g., conventional types of immunoassays. For example, a sandwich assay can be performed in which Magmas protein or a fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the anti-Magmas antibody of interest bound to the immobilized Magmas polypeptide is subsequently incubated with labeled antibody or antibody bound to a coupling agent such as biotin or avidin. Labels for antibodies are well-known in the art and include radionuclides, enzymes (e.g. maleate dehydrogenase, horseradish peroxidase, glucose oxidase, catalase), fluorescent molecules (fluorescein isothiocyanate, rhodamine, phycocyanin, fluorescamine), biotin, and the like. The labeled antibodies are incubated with the solid and the label bound to the solid phase is measured, the amount of the label detected serving as a measure of the amount of anti-urea transporter antibody present in the sample. These and other immunoassays can be easily performed by those of ordinary skill in the art.

The resultant antibody can be expressed in vivo or in vitro by a vector containing a DNA segment encoding the single chain antibody described above. These can include vectors, liposomes, naked DNA, adjuvant-assisted DNA, gene gun, catheters, etc. Vectors include chemical conjugates such as described in WO 93/04701, which have a targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector [Geller, A. I. et al., *J. Neurochem,* 64: 487 (1995); Lim, F., et al., in DNA Cloning: *Mammalian Systems, D. Glover*, Ed. (Oxford Univ. Press, Oxford England) (1995); Geller, A. I. et al., *Proc Natl. Acad. Sci: U.S.A.:*90 7603 (1993); Geller, A. I., et al., *Proc Natl. Acad. Sci USA:* 87:1149 (1990)], Adenovirus Vectors [LeGal LaSalle et al., *Science,* 259:988 (1993); Davidson, et al., *Nat. Genet* 3: 219 (1993); Yang, et al., *J. Virol.* 69: 2004 (1995)] and Adeno-associated Virus Vectors [Kaplitt, M. G., et al., *Nat. Genet.* 8:148 (1994)].

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofecton, cell microinjection, and viral vectors.

These vectors can be used to express large quantities of antibodies that can be used in a variety of ways. For example, to detect the presence of Magmas protein in a sample. The antibody can also be used to try to bind to and disrupt Magmas interaction.

The vector can be employed to target essentially any desired target cell, such as a prostate cancer cell, neuroblastoma cell, Ewings sarcoma cell, osteosarcoma cell or leukemia cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad Sci. USA* 91:2076-2080 (1994); Morrison et al., *Am. J. Physiol.* 266: 292-305 (1994)). Other methods that can be used include catheters, intravenous, parenteral, intramuscular, intraperitoneal and subcutaneous injection, and oral or other known routes of administration.

The antibody cassette is delivered to the cell by any of the known means. For example, a cassette containing these antibody genes, such as the sFv gene, can be targeted to a particular cell by the techniques described above.

The vectors may use, for example, internal ribosome entry site (IRES) sequences to force expression of the desired gene, for example, an sFv. An IRES can be used to force a stoichiometric expression of light chain and heavy chain. This forced expression avoids the problem of "silencing" where cells expressing the desired protein are phenotypically not seen, which may occur with a wide range of gene products. The IRES sequences can be used to target the single chain antibodies of interest and can be linked with a selectable marker. Selectable markers are well known in the art, e.g., genes that express protein that change the sensitivity of a cell to stimuli such as a nutrient, an antibiotic, etc. Examples of these genes include neo puro, tk, multiple drug resistance (MDR), etc.

The resultant products of that IRES linkage are not fusion proteins, and they exhibit their normal biological function. Accordingly, the use of these vectors permits the forced expression of a desired protein. Intracellular immunization strategies that are aimed at inhibiting Magmas gene expression can be RNA (antisense, ribozymes, RNA decoys) or protein (antibodies expressed intracellularly, dominant-negative mutants) based and each group of inhibitors has advantages and limitations. While RNA based strategies are often limited by the inability to achieve high levels of inhibitor expression or to allow accurate subcellular localization, protein based strategies may be limited by their potential immunogenicity. Like its normal cellular protein counterparts, the intracellularly expressed protein transgene will be degraded by the proteasome and presented on the cell surface by MHC-I to antigen presenting cells [Goldberg, A. L. Functions of the proteasome: The Lysis at the end of the tunnel. *Science* 268, 522-523 (1995); Rock, K. L. A new foreign policy: MHC class I molecules monitor the outside world. *Immunology Today* 17, 131-137 (1996)]. When the MHC-I presented peptides are recognized as foreign, a subsequent cellular immune response can be elicited against the transduced cells. Indeed, while results of several cancer gene therapy marking studies [Brenner, M. K., et al. Gene-marking to trace origin of relapse after autologous bone-marrow transplantation. *The Lancet* 341, 85-86 (1993a); Brenner, M. K., et al. Gene marking to determine whether autologous marrow infusion restores long-term haemopoiesis in cancer patients. *The Lancet* 342, 1134-1137 (1993b)] and gene replacement studies [Bordignon, C., et al. Gene therapy in peripheral blood lymphocytes and bone marrow for ADA immunodeficient patients. *Science* 270, 470-475 (1995); Blaese, R. M., et al.

Using any suitable technique known in the art, such as Northern blotting, quantitative PCR methods, etc. the level of the Magmas protein or mRNA in cells, particularly in potentially malignant cells such as prostate cells, can be measured. An increase in the level of expression of Magmas is associated with malignancy or susceptibility for malignancy.

Alternatively, the antibodies of the invention can be used in standard techniques such as Western blotting or immunohistochemistry to detect the presence of cells expressing Magmas, to quantity the level of expression.

Depending on the particular embodiment of the invention, one or more of the antibodies will be coupled with a detectable label such as an enzyme, radioactive isotope, fluorescent compound, chemiluminescent compound, or bioluminescent compound. Those of ordinary skill in the art will know of other suitable labels for binding to the antibodies or will be able to ascertain such using routine experimentation. Furthermore, the binding of these labels to the antibodies can be done using standard techniques commonly known to those of ordinary skill in the art.

For example, the antibodies can be bound to an enzyme. This enzyme, in turn, when later exposed to its substrate will react to the substrate in such a manner as to produce a chemical moiety which can be detected, as, for example, spectrophotometric or fluorometric means. Examples of enzymes that can be used to detectably label are malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, and acetylcholine esterase.

The presence of an antibody can also be detected by labeling the antibody with a radioactive isotope. The presence of the radioactive isotope could then be determined by such means as the use of a gamma counter or a scintillation counter. Isotopes which are particularly useful are $^{3}H$, $^{125}I$, $^{32}P$, $^{35}S$, $^{14}C$, $^{51}Cr$, $^{36}Cl$, $^{57}Co$, $^{58}Co$, $^{59}Fe$, $^{75}Se$, $^{99m}TC$ and $^{152}EU$.

It is also possible to detect the presence of the antibody by labeling it with a fluorescent compound. When the fluorescently labeled antibody is exposed to light of the proper wavelength, its presence can then be detected due to fluorescence of the dye. Among the most important fluorescent labeling compounds are fluorescein isothiocyanate, rhodamine, phycoerytirin, phycocyanin, allophycocyanin, o-phthaldehyde, and fluorescamine.

Another way in which the antibody can be detectably labeled is by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, aromatic-acridinium ester, imidazole, acridinium salt, and oxalate ester.

Likewise, a bioluminescent compound may also be used to label the antibody. Bioluminescence is a special type of chemiluminescence which is found in biological systems and in which a catalytic protein increases the efficiency of the chemiluminescent reaction. The presence of a bioluminescent binding partner would be determined by detecting the presence of luminescence. Important bioluminescent compounds for purposes of labeling are luciferin, luciferase, and aequorin.

The antibodies for use in the assay of the invention are ideally suited for the preparation of a kit. Such a kit may comprise a carrier means being compartmentalized to receive in close confinement one or more container means such as vials, tubes, and the like, each of said container means comprising one of the separate elements to be used in the method.

For example, one of the container means may comprise a first antibody bound to an insoluble or partly soluble carrier. A second container may comprise soluble, detectably-labeled second antibody, in lyophilized form or in solution. The carrier means may also contain a third container means comprising a detectably-labeled third antibody in lyophilized form or in solution. Such a kit can be used for sandwich assays. See, e.g., David et al. U.S. Pat. No. 4,376,110 herein incorporated by reference.

In addition, the carrier means may also contain a plurality of containers each of which comprises different, predetermined amounts of known Magmas antigen. These latter containers can then be used to prepare a standard curve into which can be interpolated the results obtained from the sample containing the unknown amount of Magmas antigen.

In one embodiment, the invention provides a method of diagnosing Alzheimer's disease (AD) in vivo comprising administering an antibody to Magmas in a suitable carrier to an individual suspected of being affected with AD and detecting the amount of Magmas in the pyramidal neurons of the hippocampus wherein decrease in the amount of Magmas compared to a normal brain indicates that the individual is affected with an AD.

In an alternative method, the antibodies of the present invention can be used to detect AD in a postmortem tissue sample comprising the pyramidal neurons of the hippocampus.

In vitro imaging can be done with the labels mentioned previously. In vivo imaging is done with diagnostically effective labeled antibodies. The term "diagnostically effective" means that the amount of detectably labeled antibody administered is sufficient to enable detection of the site of pyramidal neurons of the hippocampus when compared to a background signal. Reduction of at least about 40%, preferably about 50-60% in labeling using Magmas antibodies as compared to a control is considered as indicative of Alzheimer's disease.

Generally, the dosage of detectably labeled antibody for diagnosis will vary depending on considerations such as age, condition, sex, and extent of disease in the patient, contraindications, if any, and other variables, to be adjusted by the individual physician. Dosage can vary from 0.01 mg/kg to 2,000 mg/kg, preferably 0.1 mg/kg to 1,000 mg/kg.

The term "diagnostically labeled" means that the immunoglobulin has attached to it a diagnostically detectable label. There are many different imaging labels and methods of labeling known to those of ordinary skill in the art.

Examples of the types of labels which can be used in the present invention include radioactive isotopes and paramagnetic isotopes.

For diagnostic in vivo imaging, the type of detection instrument available is a major factor in selecting a given radionuclide. The radionuclide chosen must have a type of decay which is detectable for a given type of instrument. In general, any conventional method for visualizing diagnostic imaging can be utilized in accordance with this invention.

Another important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in a 140-200 keV range, which may be readily detected by conventional gamma cameras.

For in vivo diagnosis, radionuclides may be bound to antibody either directly or indirectly by using an intermediary functional group. Intermediary functional groups which are often used to bind radioisotopes which exist as metallic ions to antibody are diethylenetriaminepentaacetic acid (DTPA) and ethylenediaminetetracetic acid (EDTA). Typical examples of metallic ions which can be bound to immunoglobulins are $^{99m}TC$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

The antibodies used in the method of the invention can also be labeled with paramagnetic isotopes for purposes of in vivo diagnosis. Elements which are particularly useful (as in Magnetic Resonance Imaging (MRI) techniques) in this manner include $^{157}Gd$, $^{55}Mn$, $^{162}Dy$, $^{52}Cr$, and $^{56}Fe$.

Preparations of the imaging antibodies for parenteral administration include sterile aqueous or nonaqueous solutions, suspensions, and emulsions. Examples of non-aqueous solvents are propyleneglycol, polyethyleneglycol, vegetable oil such as olive oil, and injectable organic esters such as ethyloleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, antimicrobials, anti-oxidants, chelating agents, and inert gases and the like (see, Remington: The Science and Practice of Pharmacy, by Alfonso R Gennaro, ed. A. L. Gennaro, Lippincott, Williams & Wilkins; ISBN: 0683306472; 20th edition, Dec. 15, 2000).

The invention also provides a method of detecting susceptibility for cancer. Preferably the cancer is prostate cancer, neuroblastoma, Ewing's sarcoma, osteocarcinoma or leukemia. Most preferably the cancer is prostate cancer, AML or ALL. The tissue sample may be a blood sample or a biopsy of the tumor.

In one embodiment, the invention provides a method of diagnosing AML and/or ALL by using two different antibodies to Magmas. We identified several Magmas mutations in the primary diagnostic bone marrow samples from patients affected with AML and ALL. All the mutations resulted in C-terminally truncated Magmas protein. Therefore, one embodiment of the invention is directed to a method comprising providing a tissue sample, for example a bone marrow sample from an individual suspected of being affected with leukemia, providing a first antibody binding to an antigenic epitope of the N-terminal part of the Magmas labeled with a first label, for example a first fluorescent molecule, and providing a second antibody directed against an antigenic epitope of the C-terminal part of the Magmas protein labeled with a second label, for example, a second fluorescent label. Reduction in the C-terminal antibody labeling compared to a control is indicative of diagnosis of AML and/or ALL. Preferably, the diagnosis is made if the N-terminal antibody is detected in the tissue sample from an individual suspected of being affected with AML or ALL but the amount of the C-terminal antibody labeling is reduced preferably at least about 50% compared to a control sample comprising of normal bone marrow.

Because early termination often results in unstable transcripts, one embodiment of the invention is also directed to measuring Magmas transcript levels in a tissue sample from an individual suspected of being affected with AML or ALL. Reduction of the amount of Magmas transcript is indicative of the individual being affected with AML or ALL.

The expression of Magmas in the tissue sample can be analyzed by any means known to one skilled in the art. These methods include qualitative or quantitative analysis of Magmas mRNA levels or protein levels. The mRNA levels can be measured using in situ hybridization techniques as RT-PCR based quantitation methods. Antibodies can be used in a variety of immunohistochemical methods. Exemplary protocols for all the above listed methods can be found in Sambrook and Russel, MOLECULAR CLONING: A LABORATORY MANUAL, 3rd Ed., Cold Spring Harbor Laboratory Press, Cold Spring Harbor, N.Y. (2001).

To compare the expression of Magmas in a cancer sample for diagnostic or prognostic purposes, a number of control samples may be used. One can use a sample from a healthy individual or alternatively a sample from a non-asserted tissue of the individual suspected of having cancer. One can also use a panel of samples from tumors or a reference standard based upon such panel that have been determined to represent different diagnostic stages of the cancer. One example of these is the Gleason score classification of prostate cancer Gleason DF. The Veteran's Administration Cooperative Urologic Research Group: histologic grading and clinical staging of prostatic carcinoma In Tannenbaum M (ed.) Urologic Pathology: The Prostate. Lea and Febiger, Philadelphia, 1977; 171-198.

The individual has susceptibility to cancer, particularly prostate cancer, if the expression of Magmas is increased at least by about 5%, more preferably by at least about 10-50%, most preferably over 100%.

In yet another embodiment, the invention relates to a method of treating an individual affected with prostate cancer comprising the steps of administering a therapeutic Magmas blocking amount of a compound that interacts with Magmas such as, an antibody to Magmas or an antigenic epitope thereof in a pharmaceutically acceptable carrier to an individual having prostate cancer.

The invention also relates to a method of treating an individual affected with a Magmas associated cancer, such as prostate cancer, comprising the steps of administering a therapeutic cancer treating amount of Magmas-antibody-cytotoxic molecule complex in a pharmaceutically acceptable carrier to an individual having prostate cancer.

The antibody may be administered, for example, intradermally, intramuscularly, subcontaneously, or mucosally. The anti-Magmas antibodies when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 μg/kg a day, more preferably 1 to 10,000 μg/kg.

Routes of administration include oral, parenteral, rectal, intravaginal, topical, nasal, direct injection, etc.

An exemplary pharmaceutical composition is a therapeutically effective amount of an oligomer, antibody etc., that recognizes the Magmas protein, or that can induce an immune reaction against Magmas expressing cells, thereby acting as a prophylactic immunogen, optionally included in a pharmaceutically-acceptable and compatible carrier. The term "pharmaceutically-acceptable and compatible carrier" as used herein, includes one or more compatible solid or liquid filler diluents or encapsulating substances that are suitable for administration to a human or other animal. In the present invention, the term "carrier" thus denotes an organic or inorganic ingredient, natural or synthetic, with which the molecules of the invention are combined to facilitate application. The term "therapeutically-effective amount" is that amount of the present pharmaceutical composition which produces a desired result or exerts a desired influence on the particular condition being treated. For example, the amount necessary to raise an immune reaction to provide prophylactic protection. Typically when the composition is being used as a prophylactic immunogen at least one "boost" will be administered at a periodic interval after the initial administration. Various concentrations may be used in preparing compositions incorporating the same ingredient to provide for variations in the age of the patient to be treated, the severity of the condition, the duration of the treatment and the mode of administration.

One can prepare kits containing the anti-Magmas antibody or antigen. The kits would contain, for example, the anti-Magmas antibody in sterile and pyrogen free containers. Doses of the pharmaceutical compositions of the invention (e.g. the anti-Magmas antibody) will vary depending on the subject and upon the particular route of administration used. Dosages can range from 0.1 to 100,000 μg/kg per day, more preferably 1 to 10,000 μg/kg. By way of an example only, an overall dose range of from about, for example, 1 microgram to about 300 micrograms might be used for human use. This dose can be delivered at periodic intervals based upon the composition. For example on at least two separate occasions, preferably spaced apart by about 4 weeks. In the embodiment where the prime is the anti-Magmas antibody directed to the 10-25 N-terminal amino acids of the Magmas protein, with the boost of anti-Magmas antibody directed to the 10-25 C-terminal amino acids of the Magmas protein, it is presently preferred to have a series of at least 2 boosts, preferably 3 to 5 boosts spread out over a year. Other compounds might be administered daily. Pharmaceutical compositions of the present invention can also be administered to a subject according to a variety of other, well-characterized protocols. For example, certain currently accepted immunization regimens can include the following: (i) administration times are a first dose at elected date; a second dose at 1 month after first dose; and a third dose at a subsequent date, e.g., 5 months after second dose. See Product Information, *Physician's Desk Reference*, Merck Sharp & Dohme (1990), at 1442-43. (e.g., Hepatitis B Vaccine-type protocol); (ii) for example with other vaccines the recommended administration for children is first dose at elected date (at age 6 weeks old or older); a second dose at 4-8 weeks after first dose; a third dose at 4-8 weeks after second dose; a fourth dose at 6-12 months after third dose; a fifth dose at age 4-6 years old; and additional boosters every 10 years after last dose. See Product Information, *Physician's Desk Reference*, Merck Sharp & Dohme (1990), at 879 (e.g., Diphtheria, Tetanus and Pertussis-type vaccine protocols). Desired time intervals for delivery of multiple doses of a particular composition can be determined by one of ordinary skill in the art employing no more than routine experimentation.

In yet another embodiment, the invention relates to a method of diagnosing a mitochondrial disorder in an individual suspected of having a mitochondrial disorder. The mitochondrial disorder may be any mitochondrial disorder including, but not limited to, clinical manifestations such as seizures, strokes, optic atrophy, neuropathy, myopathy, cardiomyopathy, sensorineural hearing loss, diabetes meritus. The sample taken from the individual may be any tissue sample, for example, a blood sample. Magmas protein expression in the sample can be analyzed by any method well known in the art including qualitative, quantitative mRNA analysis, quantitative protein analysis, e.g. Western or dot blotting, or immunohistochemical analysis. The expression of Magmas is thereafter compared to a normal control. If the expression of Magmas is decreased in the sample from the individual compared to the control, the individual is affected with a mitochondrial disorder. The decrease in expression may vary widely because the number of affected mitochondria may vary due to known mosaicism phenomenon in mitochondrial disorders. The decrease is considered significant if it is at least about 95% of the control, preferably at least about 50-70%, even more preferably less than about 50% of the control sample. In the preferred embodiment, the analysis is an immunohistochemical analysis with an antibody directed against Magmas protein.

In another embodiment, the invention relates to a method of determining the severity of a mitochondrial disorder comprising the steps of taking a biological sample of an individual suspected of having a mitochondrial disease, analyzing the Magmas protein expression in the sample, comparing the expression of the Magmas protein in the sample to a normal sample and/or comparing the expression of the Magmas protein in the sample to expression in a panel of samples consisting of tissue samples representing different degrees of severity of a mitochondrial disorder. The expression profile of the Magmas protein in the sample indicates the stage of mitochondrial disorder and provides prognostic information and guidance that can be used, for example in designing treatment options. For example, an individual with less than 50% of the normal Magmas expression is considered more severely affected than an individual with about 95% of the normal Magmas expression.

The invention further provides a method of diagnosing AML and /or ALL by identifying truncation of the Magmas protein. More specifically, the invention provides identification of one or more of the following mutations:

MAKYLAQIIVMGVQVVGRVFARALRQEFAFARALRQEFAELZ, a frameshift deletion of 46 codons at intron/exon site(SEQ ID NO: 5), results in 41 amino acid protein);

MAKYLAQIIVMGVQVVGRAFARALRQEFAASRFQPLRPQPPGGTADSQRVQAEPZ (SEQ ID NO: 6), deletion of 14 codons results in 54 amino acid protein;

MAKYLAQIIVMGVQVVGRAFARALRQEFAASRRHSRFSTCPSZ (SEQ ID NO: 7), frameshift deletion of 22 codons results in 44 amino acid protein;

MAKYLAQIIVMGVQVVGRAFARALRQEFAASTPZ (SEQ ID NO: 8), a 174 bp insert results in truncated 32 amino acid protein instead of 125 aa protein; and MAKYLAQIIVMGVQVVGRAFARALRQE-FAASRAEADARGRAGHRSAAASNLSGLSLQ EAQQKNYEHLFKVNDKSVGGSFYLQTKV-VRAKERLDEELKIQAQEDRKKGQMPHTZ (SEQ ID NO 9), a deletion of 13 amino acids, numbers 62-74 results in 112 amino acid protein. In one embodiment, the variation results in a frameshift causing a downstream truncation of amino acid 29 of SEQ ID NO: 4 and the disease condition is AML or ALL.

Most of the molecules known to be involved in GM-CSF mediated signal transduction are also involved in IL-3 signaling. The a subunit of the receptor complex determines ligand specificity and is required for IL-3 and GM-CSF signal transduction. Studies with hybrid receptors constructed with the cytoplasmic domains of the murine IL-3 receptor showed that only αβ heterodimers generated a mitogenic response [18]. Homodimers of either α or β cytoplasmic domains were without activity. Mutagenesis of the cytoplasmic portion of the GM-CSF or IL-3 receptor α subunit suggested that specific regions of the receptor were important for proliferation, differentiation and survival [19-22].

While a few studies have described molecular differences between GM-CSF and IL-3 signal transduction pathways, most have shown them to be identical. We have identified a novel mitochondrial associated protein named Magmas whose role in GM-CSF activity in a murine myeloid cell line differs from that of IL-3. Differential display was used to compare the mRNA expression of PGMD1 cells cultured in GM-CSF to those cultured in IL-3. Using this approach we isolated a novel mitochondrial associated gene, Magmas, whose message level was induced by GM-CSF. Consistent with its induction by GM-CSF, the promotor for Magmas contains an AP-1 binding site which is known to be GM-CSF responsive [33], and a MZF-1 [34] binding motif which is important in neutrophil development [35].

The mouse and human forms of Magmas protein are highly homologous. 120/125 amino acids comprising the mature protein are identical, and those that differ are generally conservative amino acid changes. The protein has a leader sequence which targets it to the mitochondria, as demonstrated by immunohistochemistry and localization of GFP tagged protein. Although sequences that target proteins to the mitochondria vary, the signal sequence of Magmas shares the characteristic amino acid composition of positively charged residues interspersed among hydrophobic residues [36, 37]. The Magmas leader sequence is incompatible with those sequences that result in import into, or retention in the endoplasmic reticulum (includes golgi, lysosome, endosome and secretory vesicles), import into the nucleus, import into peroxisomes, or attachment to membranes [38, 39].

The large 1st intron following the short 1st exon is not a feature common to many genes. This indicates that the intron has a regulatory role such as permitting the down stream methionine in the second exon to act as a translational initiation site. The detection of the Magmas doublet on Western blot is compatible with initiation occurring at both of these start sites. Initiation at the more distal site results in a protein lacking a complete mitochondrial targeting sequence, which could potentially alter its localization and activity.

Results from Northern tissue dot blot showed that Magmas mRNA was expressed in all tissues in variable amounts. The highest levels were observed in heart, skeletal muscle and pituitary gland. mRNA levels in fetal tissues were not as high as those in the corresponding adult tissues, implying that expression could be differentiation but not proliferation dependent. Significantly, many of the tissues with high Magmas mRNA levels by dot blot are not believed to express GM-CSF receptor. Consequently, Magmas expression is also influenced by other transduction pathways besides those regulated by GM-CSF.

GM-CSF induced Magmas mRNA expression in PGMD1 cells which had been growing in IL-3, we determined whether increased or reduced Magmas protein levels would affect the ability of these cells to respond to either growth factor. Full length sense and anti-sense cDNA was transfected into PGMD1 cells and protein levels were measured by Western blot. Compared to wild type cells, cells with overexpression of Magmas had similar proliferative rates and dose responsiveness in GM-CSF and IL-3. In contrast, cells with reduced Magmas proliferated poorly in GM-CSF. This effect was specific because the growth of these cells in IL-3 was comparable to the wild type and sense transfected cells (the latter also serves as the vector control). However it is not known if Magmas is required for growth of PGMD1 cells in IL-3 since we have not identified any clones completely lacking expression of the protein.

Although not wishing to be bound by theory, there are several theories that account for the activities of Magmas in PGMD1 cells. The first is that Magmas affects the expression/activity of the GM-CSFreceptor or is involved in pathways activated by this receptor. An example of a protein having the latter characteristic is fps/fes, a cytoplasmic tyrosine kinase. In mice with homozygous fps/fes kinase inactivating mutations, growth factor stimulated phosphorylation of Stat 3 and Stat 5A was impaired for GM-CSF but not IL-3 [40]. It does not seem likely that Magmas regulates receptor expression or interacts in the known signal transduction pathways at this level because of its mitochondrial location as well as its lack of homology to transcription factors or to cytoplasmic or membrane proteins.

Another possibility is that Magmas acts as an inhibitor of programmed cell death. Magmas has several features in common with Mcl-1, a bcl-2 family member. Both are induced by GM-CSF [41], have a wide tissue distribution [42], and co-localize with the mitochondrial compartment [43]. The lack of an apparent phenotype of PGMD 1 cells with poor Magmas expression grown in IL-3 may result from an analogous protein specific for IL-3, or from the loss of responsive clones during post transfection culture. However, most inhibitors of apoptosis are not growth factor specific and Magmas does not have the BH4 domain or any other homology to these proteins.

Magmas can also be an important regulator of mitochondrial activity and therefore cell metabolism. A role in energy metabolism would explain the divergent effect that reduced protein levels have on cells cultured in GM-CSF and IL-3. Although influenced by receptor expression, IL-3 and GM-CSF appear to differ in their ability to stimulate a respiratory burst in neutrophils [44-46], and mononuclear cells [47-49]. The GM-CSF stimulated respiratory burst is characterized by the generation of toxic oxygen derivatives such as hydrogen peroxide and superoxide [50]. GM-CSF is sufficient for the respiratory burst in adherent neutrophils while those in suspension require an additional signal which experimentally is usually FMLP [46].

The respiratory burst is one component of the neutrophil activation process which also includes increased glucose transport [51-53], increased glycolysis and $Na^+/H^+$ antiporter activity [54], enhanced phagocytosis and antibody mediated cytotoxicity [55]. It is likely that GM-CSF and IL-3 have dissimilar activities on other aspects of the neutrophil activation process in addition to respiratory burst, but few definitive experiments have been performed. Recently, using the yeast 2-hybrid system, a protein has been identified which associates with GM-CSFα subunit but not the IL-3α subunit [56]. This protein named GRAP, affects glycogen accumulation in yeast and may be involved in some of the divergent effects that IL-3 and GM-CSF have on cellular metabolism. Similar to Magmas, GRAP was found to be expressed in all cell types.

Our data indicates that Magmas is involved in cell metabolism. Magmas is associated with mitochondria and has high message levels in metabolically active, non-proliferating, tissues such as muscle, adrenal gland, testis and liver. In PGMD1 cells with reduced Magmas expression, growth appears normal in IL-3 but not in GM-CSF. Induction of Magmas message by GM-CSF could be a compensatory response to the energy requirement of the cell. Low Magmas levels should have similar effects on eosinophils grown either in GM-CSF or IL-3, since both of these HGF have similar activating activities on these cells [57, 58].

Assays to further study Magmas exact role in mitochondrial activity and GM-CSF signaling in hematopoietic cells can look at mitochondrial membrane permeability, electron transport and redox potentials, and its potential interactions with proteins such as channel proteins, caspases, proteolytic inhibitors, and other members of growth factor signal transduction pathways.

We have now discovered that the level of expression of Magmas is associated with cancer. Examples of cancers associated with Magmas over expression include, but are not limited to prostate cancer, neuroblastoma, Ewings sarcoma, osteosarcoma and leukemia. Prostate carcinoma, one of the several malignancies known to express the GM-CSF receptor or respond to GM-CSF, was examined for Magmas expression. Normal prostate stained slightly less strongly than benign hyperplasia which was less that the carcinoma samples. This was even true for the various histological grades found within a single tumor. Pathologic grading of tumor samples revealed that Magmas expression closely correlated to the Gleason score. The level of Magmas expression also parallelled the level of GM-CSF receptor detected by immunohistochemistry, suggesting a functional relationship.

In human prostate, several publications have shown little difference between the mitochondria in normal prostate tissue and those in differentiated carcinoma (Kumamoto Medical J 20:. In contrast, in undifferentiated carcinoma, mitochondria were reported to be more numerous and had a more variable morphology. Unfortunately none of these studies normalized mitochondria content to cell size, making a direct comparison of these organelles very difficult. In hepatocellular carcinoma, the differences in the number of mitochondria/cell was related to the size of the cell.

The results of the electron microscopy showed that the mitochondria content did not significantly vary between normal and malignant prostate in agreement/disagreement with a previous study. EM was used to quantitate the mitochondrial content of the cells because of the uncertainly (that a particular protein is better) there are no better markers available. Importantly, the amount Magmas/mitochondria was increased in the tumors compared to the normal prostate. This demonstrates that Magmas is increased and does not simply reflect the mitochondrial content of the cell.

The role of Magmas in the pathogenesis, progression or maintenance of the malignant phenotype in prostate cancer is unclear. Although there are no published reports showing chromosomal translocations involving 16p13.3 in prostate cancer, linkage analysis suggests that the entire arm of 16p could be involved in an increased susceptibility (Prostate 45:106-114, 2000). Some cancer cells have been reported to have increased anaerobic metabolism compared to their normal counterparts. It is possible that abnormal Magmas expression or activity may lead reduced aerobic metabolism by inhibiting the production of ATP. A potential mechanism of action is suggested by co-immunoprecipitation studies and experiments with the yeast two hybrid system demonstrating an interaction between Magmas and the adenine nucleotide translocator 3 (ANT). ANTs, found in the inner membrane of mitochondria, mediate ADP/ATP exchange and have a role in oxidative phosphorylation and apoptosis.

The invention also provides a polymorphism (glutamine/lysine at position 114 of the human gene) in the Magmas gene that is strongly associated with predisposition to prostate cancer. This polymorphism can be identified in about 50% of prostate cancer patiens whereas in normal population, the prevalence is only about 3-4%. Therefore, this polymorphism is useful in detecting individuals who may be predisposed to prostate cancer and require more frequent follow-up than individuals without the polymorphism.

The invention further provides specific mutations in the Magmas. We have identified a point mutation in the Magmas gene in a patient with a mitochondrial disorder having phenotypic features including developmental delay, hypotonia, ataxia, progressive limb weakness, exercise intolerance, myoclonus, failure to thrive and seizures. This mutation decreases the expression of Magmas which assists in diagnosis as well as prognostics of the mitochondrial disorders. The point mutation A->G results in a mutation E72G.

We have additionally identified several mutations in patients with AML and ALL. These mutations include:

MAKYLAQIIVMGVQVVGRVFARALRQE-FAFARALRQEFAELZ, a frameshift deletion of 46 codons at intron/exon site(SEQ ID NO: 5), results in 41 amino acid protein);

MAKYLAQIIVMGVQVVGRAFARALRQE-FAASRFQPLRPQPPGGTADSQRVQ AEPZ (SEQ ID NO: 6), deletion of 14 codons results in 54 amino acid protein;

MAKYLAQIIVMGVQVVGRAFARALRQE-FAASRRHSRFSTCPSZ (SEQ ID NO: 7), frameshift deletion of 22 codons results in 44 amino acid protein;

MAKYLAQIIVMGVQVVGRAFARALRQEFAASTPZ (SEQ ID NO: 8), a 174 bp insert results in truncated 32 amino acid protein instead of 125 aa protein; and MAKYLAQIIVMGVQVVGRAFARALRQE-FAASRAEADARGRAGHRSAAASN LSGLSLQEAQQKNYEHLFKVNDKSVGGS-FYLQTKVVRAKERLDEELKIQAQ EDRKKGQMPHTZ (SEQ ID NO 9), a deletion of 13 amino acids, numbers 62-74 results in 112 amino acid protein.

These mutations are useful in diagnosis of leukemia. For example, the mutations can be screened for in a tissue sample, preferably in a bone marrow sample obtained from an individual suspected of having leukemia. Detection of these mutations can be performed using methods well known to one skilled in the art. Such methods include PCR-based methods, wherein nucleic acid, i.e. either DNA or RNA, in the sample is amplified using primers flanking the mutation site. The difference in the size or the sequence of the amplified nucleic acid is detected using gel electrophoresis and/or nucleic acid sequencing and/or any other method capable of differentiating between size or sequence in the amplified nucleic acid. Methods routinely used by one skilled in the art in such application are presented, for example, in Sambrook and Russel, MOLECULAR CLONING: A LABORATORY MANUAL, 3rd Ed., Cold Spring Harbor Laboratory Press, Cold Spring Harbor, N.Y. (2001), the entirety of which is herein incorporated by reference.

EXAMPLE

Cell lines and culture. PGMD1, a murine factor dependent myeloid cell line [23], was maintained in hybridoma media (Sigma, St Louis, Mo.) supplemented with 15% FCS (Sigma) and murine IL-3 (10 ng/ml; Preprotech, Princeton N.J., or Sigma). Magmas sense and antisense DNA in the vector pREP4 (Invitrogen, San Diego, Calif.) was transfected into PGMD1 cells by electroporation (260 volts, 960 μF; Gene Pulser, BioRad, Hercules, Calif.). Immediately after electroporation, the cells were plated in microwell dishes, and two days later were selected by culture in hygromycin (375 units/ml, Calbiochem, San Diego, Calif.). Statistically most wells contained a single colony. Magmas-green fluorescent protein fusion protein (linked 5' Magmas-GFP3') and green fluorescent protein (GFP) (EGFP, Clontech, Palo Alto, Calif.) alone were also expressed in PGMD1 cells using pREP4 and identical techniques.

Differential Display. PGMD1 cells exponentially proliferating in IL-3 were washed 3 times in warm GM-CSF containing media and then cultured in murine GM-CSF (40 ng/ml; gift from Genetics Institute, Cambridge Mass.). RNA was prepared using RNAzol B (Biotecx, Houston, Tex.) and MessageClean (GenHunter, Nashville Tenn.) from cells grown in IL-3 (T=0 hr) or in GM-CSF for 6, 12, or 24 hours. cDNA reverse transcribed from the polyA mRNA was amplified by PCR using differential display primers and reagents (GenHunter) and 35S dATP (NEN, Boston, Mass.). The resulting products were subjected to polyacrylamide gel electrophoresis and the results from each time point were analyzed after autoradiography. Each reaction was performed on RNA isolated from three independent experiments. Fragments which showed consistent changes over the three experiments were excised from the gel, and cloned into the pCR-TRAP vector (GenHunter). The sequence of each fragment was determined by automated DNA sequencing using standard techniques.

Northern Hybridization. Total RNA was prepared (Rneasy, Qiagen, Valencia, Calif.) from PGMD1 cells grown in murine IL-3 or murine GM-CSF (PeproTech) for the time periods indicated. 10 μg total RNA per lane was fractionated on a 1% agarose formaldehyde gel at 75 volts for 3 hours [24]. After overnight upward transfer in 20× saline sodium citrate (SSC; 150 mM NaCl/15 mM Sodium Citrate) to Duralon-UV membrane (Stratagene, LaJolla, Calif.) the RNA was crosslinked (UV Stratalinker 2400) and stained with methylene blue to confirm uniformity of loading and transfer. Magmas and glyceraldehyde 3-phosphate dehydrogenase (GAPDH) probes were radiolabeled with $^{32}$P dCTP (NEN, Boston, Mass.) using random primers (HighPrime, Roche, Indianapolis, Ind.) and then column purified (ProbeQuant G-50, Pharmacia, Piscataway, N.J.). After hybridization (QuickHyb, Stratagene, La Jolla, Calif.) overnight at 68° C., the blots were washed twice in 2×SSC/0.1% sodium dodecyl sulfate (SDS) and twice in 0.1×SSC/0.1% SDS, and exposed to film. Northern blots were performed on RNA isolated from three independent experiments.

A multiple tissue array dot blot was probed with a random primer $^{32}$P dCTP labeled Magmas probe or a ubiquitin control probe with ExpressHyb hybridization solution block, according to manufacturers directions (Human MTE Array, Clontech). After a 3 day exposure on a phosphoimager plate the data was analyzed using ImageQuant 1.2 on a Storm 860 Phosphoimager (Molecular Dynamics, Sunnydale, Calif.). The entire listing of mRNA samples on the membrane can be found at 2001 Catalog by Clontech.

Cloning of cDNA and genomic DNA. A cDNA library was prepared from mRNA isolated from PGMD1 cells cultured for 48 hours in GM-CSF. 10 ng of cDNA was converted to double stranded DNA by nick translation and ligated into the pSport vector (Superscript plasmid system, Life Technologies, GIBCO BRL, Gaithersburg, Md.). An oligonucleotide probe (gagcgtccgccatggccaagta) [SEQ ID NO: 1] derived from the differential display fragment sequence was used to isolate the murine cDNA clone using the GeneTrapper cDNA positive selection system (GIBCO BRL). The method consists of degradation of one strand of the library plasmids with exonuclease III; solution hybridization with the specific biotinylated oligonucleotide probe; capture of positive clones on streptavidin beads; and priming and repair of the plasmid to double strandedness. Selected clones were screened for inclusion of the differential display fragment sequence. The translational start site, leader sequence and regions of interest were identified by SMART [25, 26], (Simple Modular Architecture Research Tool). The GenBank accession number assigned to murine Magmas is AF349454.

Human Magmas cDNA and genomic DNA were cloned from peripheral blood cell by PCR using primers designed from comparing the mouse cDNA and a human cosmid clone sequence found in GenBank 5' and 3' untranslated regions of human T2c12 cDNA were cloned by the RACE method [27, 28], using a series of primers selected by the Oligo program (Molecular Biology Insights, Cascada, Colo.). The human Magmas GenBank accession number is AF349455. Transcription factor binding sites were identified by the TFSEARCH program utilizing the TRANSFAC database [29].

Polyclonal Antibody. Mixtures of human and murine peptides comprised of the 19 amino-terminal (N-terminal) terminal or 20 carboxy-terminal (C-terminal) amino acids were synthesized and coupled to KLH (Dana Farber Cancer Institute Core Facility, Boston, Mass.) and inoculated into rabbits (Covance, Richmond, Calif.). The antibodies were generated using fragments having the N-terminal amino acid sequence:

```
DEEL(R/K)IQAQEDREKGQ(K/L)P(K/H)T    [SEQ ID NO: 2]
```

and a C-terminal amino acid sequence:

```
RALRQEFAAS(Q/R)AAADARGRC.     [SEQ ID NO: 3]
```

Antisera and the preimmune sera were screened against lysates from bacterial clones expressing murine Magmas, human Magmas or a non specific similar sized control protein by Western blot. For immunohistochemistry, the immune, preimmune, and control (from rabbits injected with a nonreactive KLH coupled peptide) sera were purified on a HiTrap protein G column (Amersham Pharmacia Biotech, Piscataway, N.J.). The concentration of the eluted protein was measured by the Bradford method (BioRad) using immunoglobulin as the protein standard.

Immunohistochemistry. Cytospin prepared slides were blocked in PBS containing 1.5% BSA and 2% non fat dry milk. The slides were then incubated in purified immune and control antibody (10 ng/ml) in PBS/BSA for 1 hr at 37° C., washed and incubated with FITC conjugated anti-rabbit antibody. After 3 rinses, the slides were counterstained with Vectorshield with propidium iodide (Vector Laboratories, Burlingame Calif.), and examined under fluorescent microscopy. Subcellular fractionation of mitochondria was achieved by dounce homogenization and differential separation through 0.25 M sucrose, using the succinate dehydrogenase assay as the marker [30].

Human prostate tissue was obtained from surgical prostatectomy samples or archival blocks with the approval of the Institutional Review Boards of Children's Hospital Medical Center and the University of Cincinnati Medical School. The prostate samples for morphology and light immunohistochemistry were fixed in paraformaldehyde, dehydrated in ethanol containing solutions, embedded in paraffin and sectioned. Slides from each sample were stained with H and E and graded according to the Gleason classification.

Magmas expression was determined by incubating the samples in protein G purified polyclonal anti-Magmas antibody or control antibody (10 ng/ml) followed by biotinylated goat anti-rabbit IgG (Vector Laboratories, Burlingame, Calif.) and streptavidin congugated horse radish peroxidase (Dako, Carpinteria, Calif.). The slides were then incubated with diaminobenzidine (DAB) solution (Dako). Similarly to detect the GM-CSF receptor expression, sectioned tissues were sequentially incubated in anti-GM-CSF receptor a or isotype control antibody (both at 10 μg/ml), horse radish peroxidase conjugated anti-rabbit IgG and DAB, (Ventana Medical Systems, Tucson, Ariz.). The results of histological grading and the scoring were done independently and blinded.

Magmas expression was determined by incubating the samples with anti-Magmas antibody or control antibody followed by biotinylated goat anti-rabbit IgG. Similarly, human tissues were sequentially incubated in anti-GM-CSF receptor$\alpha$ subunit antibody (Alpha Diagnostics, San Antino, Tex.) or isotype control antibody (Sigma), anti-rabbit IgG-horse radish peroxidase and All slides were counter-stained with Mayers hematoxylin.

The electron microscopy samples processed as previously described. Normal and malignant prostate tissue were fixed in 4% paraformaldehyde/2.5% glutaraldehyde followed by fixation in 2% osmium tetroxide (Electron Microscopy Sciences, Ft. Washington, Pa.) reduced with 1.5% potassium ferrocyanide both in Hank's Balanced Salt Solution containing 5% sucrose. After dehydration, and embedding in Eponate (Ted Pella, Redding, Calif.), the tissue was sectioned and placed on mesh nickel grids (Electron Microscopy Sciences) [31]. Next the grids were incubated with anti-Magmas antibody or control antibody followed by biotinylated goat anti-rabbit IgG (KPL Laboratories, Gaithersburg, Md.), and streptavidin:5 nm gold colloid [32]. The samples were then stained with 2% aqueous uranyl acetate (Electron Microscopy Sciences) and viewed in a JEOL 100CX II electron microscope. The distribution and location of the gold grains/micron$^2$ was determined by stereologic analysis using the point counting method [33]. The samples were scored as the number of grains/micron2 of mitochondria and the of area of mitochondria divided by the total area of sample.

Western Blot. Equal numbers of PGMD1 cells and cells expressing GFP or a Magmas-GFP fusion protein were solubilized in Laemmli sample buffer and the proteins were separated by SDS-PAGE. The proteins were transferred to a nitrocellulose membrane (TransBlot Transfer Medium, Biorad) in a Tris/Glycine-20% methanol solution overnight (100 volt-hr) at 4° C. [31]. Membranes were rinsed, blocked and then incubated with anti-Magmas antisera (1/500). After washing, the membrane was immersed for 30 minutes with peroxidase-labeled secondary antibody (1/10,000), washed four times with large volumes of buffer containing 50 mM Tris pH 7.5/150 mM NaCl/0.1% Tween 20 (TBST), for 15 minutes each, developed in luminol substrate and exposed to film (BM Chemiluminescence Western Blotting Kit, Roche Molecular Biochemicals, Indianapolis, Ind.). The blot was then stripped and similarly reprobed with a mixture containing preimmune sera and rabbit anti-GFP antibody. Kaleidoscope Prestained Standards (BioRad) were used for molecular weight determinations. Relative loading of the lanes was confirmed by Ponceau S (Sigma) staining of the membrane [32].

Proliferation assay. After washing 3 times, PGMD1 cells were plated at 6000 cells/well and cultured at 37° C. for 72 hrs in 160 μl media containing 15% FCS without factor, or with varying concentrations of IL-3 or GM-CSF as indicated. The cells were then cultured for an additional 4 hours with 1 μCi/well of $^3$H thymidine (NEN), harvested using a FilterMate Harvester and counted on a TopCount Microplate Scintillation Counter (Packard, Meriden, Conn.). Each time point is the mean of three wells, and each experiment was performed twice.

Expression of Magmas message in tumor and normal prostate tissue. A multiple tissue array dot blot consisting of RNA derived cDNA was used to determine Magmas mRNA expression from malignant and normal prostate tissue from the same patient (Matched Tumor/Normal Expression Array, BD Biosciences Clontech). The cDNA on the membrane, which accurately reflects the relative abundance of mRNA, have been normalized by the manufacturer to ubiquitin, ribosomal protein S9 and 23 kD highly basic protein. The membrane was probed with a random primer 32P dCTP labeled Magmas probe or a GAPDH control probe with ExpressHyb hybridization solution block, according to manufacturer's directions (Human MTE Array, Clontech). After a 3 day exposure on a phosphoimager plate the data was analyzed using ImageQuant 1.2 on a Storm 860 Phosphoimager (Molecular Dynamics, Sunnydale, Calif.).

Figure 1:
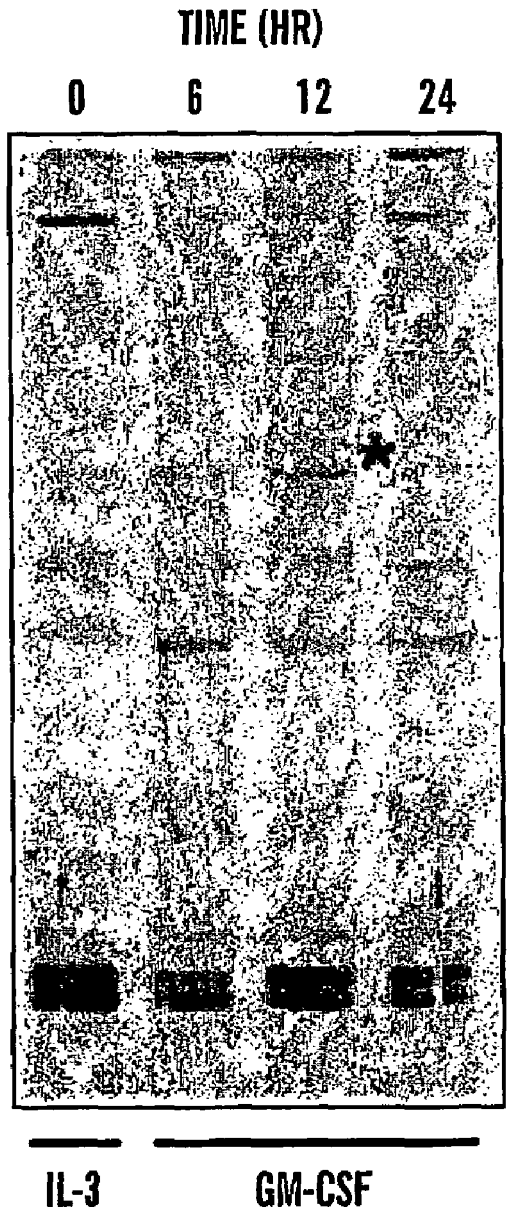
FIG. 1 shows a gel electrophoresis of differential display products from PGMD1 cells grown in the presence of IL-3 or GM-CSF. PGMD1 cells were cultured in the presence of IL-3 (t=0) or GM-CSF for 6, 12 or 24 hours and the resulting RT-PCR products were separated using polyacrylamide gel electrophoresis. The star (*) to the right of the band at t=12 hr indicates the DNA fragment which was used to isolate Magmas. Representative of three experiments.

Differential expression of PGMD1 mRNA from cells cultured in IL-3 and GM-CSF. The growth factor dependent cell line PGMD1 was used to identify genes that were differentially responsive to IL-3 and GM-CSF. RNA isolated from exponentially proliferating cells grown in IL-3 (T=0) or cells cultured for 6, 12, and 24 hours in GM-CSF, was analyzed by differential display. After amplification by PCR the products were subjected to polyacrylamide gel electrophoresis and the PCR fragments compared at the different time points. The increased number of PCR fragments observed when the cells were grown in GM-CSF was typical for many of the primer sets used during the amplification step. Thirty five PCR fragments showing differential expression at the various time points were cut out of the gel and cloned. An autoradiograph of the differential display gel containing the PCR product from which a fragment of Magmas was isolated is shown in FIG. 1. To the left of the star is the band which encodes a fragment of Magmas cDNA.

Figure 2:
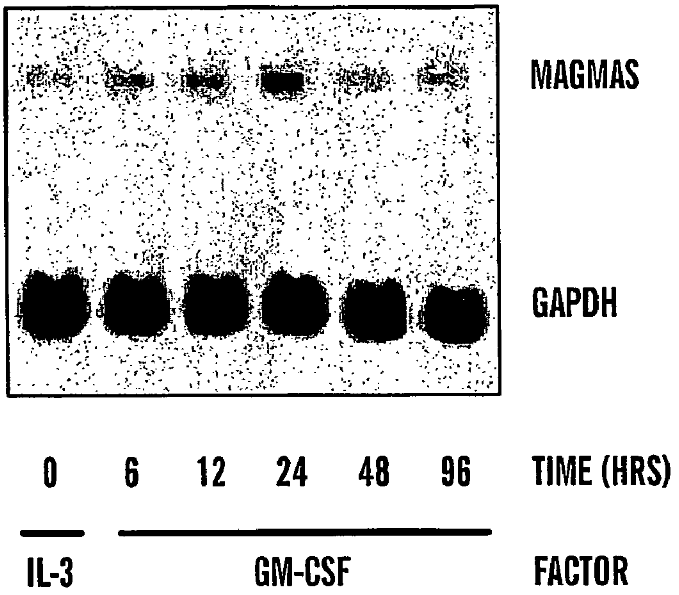
FIG. 2 shows a Northern blot hybridization analysis of Magmas expression in PGMD1 cells. mRNA prepared from cells cultured in IL-3 or for 6, 12, 24, 48 or 96 hours in the presence of GM-CSF was resolved by agarose gel electrophoresis and transferred to a nitrocellulose membrane. The membrane was first hybridized with a DNA probe to Magmas and then stripped and hybridized with a probe to GAPDH which was used as the control for loading. Representative of three experiments.

Message levels are regulated by GM-CSF. To confirm that the cDNA fragments identified by differential display had variable levels of mRNA expression when the cells were cultured in IL-3 or GM-CSF, Northern blot analysis was performed using probes derived from the cloned fragments. Fourteen of the 35 fragments selected for further analysis were found to have variable expression over time. As shown in FIG. 2A, one of the genes which had a single transcript size of approximately 500 kb was weakly expressed in PGMD1 cells grown in IL-3 (T=0). After 6 hours of culture in GM-CSF, the amount of transcript was increased. Transcript level continued to rise to a maximum of approximately 5-6 fold at 24 hours of GM-CSF exposure. At T=48 and 96 hr the transcript level was lower than that seen at T=24, however it was still higher than the amount detected in cells growing in IL-3. The blot was then stripped and re-probed with DNA complimentary to GAPDH (FIG. 2B) as a control for sample loading and transfer. Consistent with methylene blue staining prior to hybridization, the GAPDH signal was approximately equal in every lane. These results demonstrate that GM-CSF was able to induce Magmas transcript levels over those observed when PGMD1 cells are grown in IL-3.

Gene and Protein Structure. A murine cDNA library derived from PGMD1 cells grown in GM-CSF was used to isolate the Magmas gene. Clones were selected from the library using an oligonucleotide probe based on the differential display fragment sequence. The cDNA isolated was 536 bp in length and contained the original differential display DNA fragment at the 3' end (FIG. 3A). The clones consisted of a 78 bp 5' untranslated region, a 375 bp open reading frame and an 83 bp 3' non coding segment.

After characterizing the murine cDNA, the Genbank database was searched for a human equivalent. BLAST comparison to the murine Magmas sequence yielded a single match with 87% homology to regions of a human cosmid clone RT140 (AC004789) located on chromosome 16p13.3. Despite the high degree of homology to the murine cDNA sequence, the equivalent translational start site for the human homolog was not readily apparent from examination of the genomic sequence.

To determine the sequence of the N terminal portion of the human gene, we used internal primers to amplify the 5' and 3' untranslated regions of human cDNA by the RACE method. The sequence of human cDNA was identical to discontinuous regions in the human genomic clone. The intron-exon boundaries conform to the GT/AG rule for the splice donor and acceptor sites. There is a typical translational start site consisting of a Kozak sequence and fmet initiation codon. Binding sites for transcriptional factors AP-1, GATA1, GATA2, GATA3, Ik-1, AML-1a, MZF-1 and c-Ets are located upstream of the transcriptional start site. Based upon the human cDNA sequence and genomic sequence the human gene is comprised of 5 exons and 4 introns and contains 12,975 bases (FIG. 3B). Interestingly, the first exon consists of just the 5' untranslated region and the fmet codon and is separated from the second exon by a 9.9 kb intron.

The protein predicted for Magmas consists of 125 amino acids including a 21 residue leader sequence identified by the SMART protein analysis program (FIG. 3B). The leader sequence consists of many hydrophobic amino acids, a few basic amino acids and no acidic residues, and is only consistent with sequences that target proteins to the mitochondria. Although the protein did not contain any known functional domains there were two regions of low compositional complexity identified at the N terminus (aa 23-41 and 45-56) and a region having some similarities to a DnaJ domain (aa 57-110). In the absence of any postranslational modification, a protein initiated at the first start site would have an expected molecular weight of 13.7 kd. A comparison of the coding regions of the human and murine genes showed amino acid differences only at positions 32, 41, 110, 122 and 124 (FIG. 3A). A polymorphism resulting in a change from glutamine to lysine at position 114 has also been detected in the human sequence.

Figure 4:
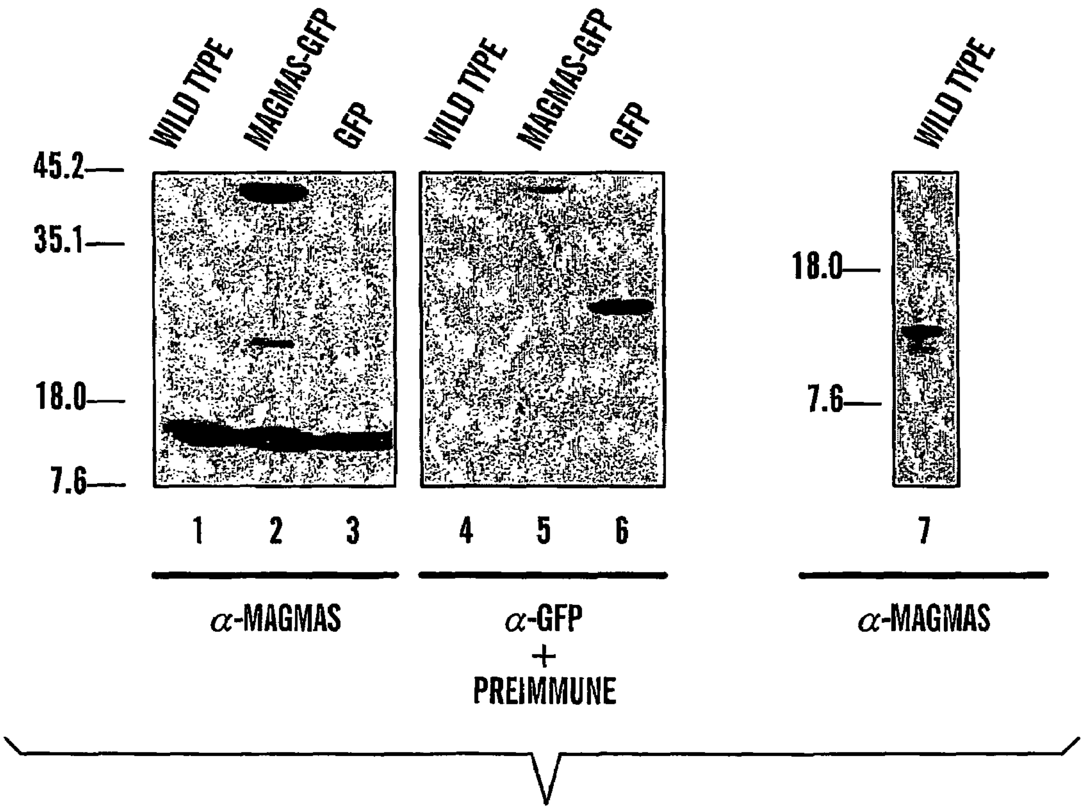
FIG. 4 shows the molecular weight determination of Magmas by Western blot. Protein extracts from wild type PGMD1 cells (lanes 1,7) and cells expressing Magmas-GFP fusion protein (lane 2) or GFP (lane 3) were separated by SDS-PAGE, transferred to nitrocellulose membranes and incubated with anti-Magmas antisera After incubating with peroxidase labelled anti-rabbit Ig and chemilumenescent reagent the blot was exposed to film and the autoradiograph developed. The blot (containing lanes 1-3) was stripped and reprobed with preimmune sera and anti-GFP antibody (lanes 4-6) in a similar manner. Representative of two experiments.

The molecular weight of the native protein was estimated by Western blot analysis (FIG. 4). Lysates from wild type PGMD 1 cells or controls (cells transfected with constructs encoding a Magmas-GFP fusion protein or GFP alone) were subjected to polyacrylamide gel electrophoresis, transferred to nitrocellulose and blotted with antibody against Magmas (lanes 1-3). After incubation with peroxidase coupled anti-rabbit antibody and addition of chemiluminescent reagent, the blot was exposed to film. In lane 1 (wild type cells), a major fragment having a molecular weight of approximately 13 kD was observed. This correlates with the molecular weight predicted from the amino acid sequence. Cells transfected with the Magmas-GFP fusion protein (lane 2) had two major fragments. The lower corresponds to the endogenous Magmas protein seen in lane 1 while the upper has the expected molecular weight of the fusion protein. The cells containing the construct encoding only GFP were similar to the wild type cell sample when blotted with the anti-Magmas antisera (lane 3).

The blot was then stripped and re-probed with a mixture of control preimmune sera and antibody against GFP (lanes 4-6). Under these conditions the lower band was no longer present in any of the lanes. This demonstrates that anti-Magmas serum specifically recognizes the 13 kD protein. When the cells transfected with the fusion protein construct were blotted with the anti-GFP/preimmune sera mixture (lane 5) a high molecular weight band identical to the one in lane 2 was observed. This together with the result seen in lane 2 conclusively proves that the 13 kD protein seen in lanes 1-3 is Magmas. In lane 6, (cells transfected with GFP alone) a single band having the expected molecular weight of GFP (27 kd) was visualized, confirming the specificity of the anti-GFP antibody.

When PGMD1 cell lysates were separated on a higher resolution polyacrylamide gel the Magmas protein fragment was shown to consist of a doublet having molecular weights of 11,460 and 12,820 daltons (lane 7) on Western blot. The former corresponds very favorably to the molecular weight of the Magmas with a cleaved signal peptide (11,530 daltons) and the latter to a Magmas protein initiated at the distal methionine residue (12,650 daltons). The difference in size appears too small for the fragments to represent the protein with or without the leader sequence. Occasionally a fragment of approximately 25 kD has been seen on Western blot of whole cell lysate. The blot used in FIG. 4 provides the most prominent example of this fragment (lane 2, middle band). Unlike Magmas, this band is not immunopreciptated by the polyclonal antibody to Magmas and does not bind to an anti-Magmas immunoaffinity column (data not shown). This demonstrates that the responsible epitope is only recognized when the protein is in a denatured state. The exact nature of the 25 kd band is unknown but the possibilities include a protein derived from another transcript, a post-translational modification of Magmas, or a protein containing a cross-reacting epitope.

Expression of Magmas mRNA in tissues. A Northern dot blot containing RNA derived from a variety of human tissues was used to determine the tissue distribution of Magmas. To get the best approximation of relative mRNA levels, the amount of poly $A^+$ mRNA loaded for each tissue was normalized to 8 different housekeeping genes by the manufacturer. A quantitative measure of Magmas mRNA expression was obtained by phosphoimager analysis. The mean signal volume for all of the human tissues was 6644 with a standard deviation (n−1) of 6377. Every tissue on the blot had a detectable amount of message. The volumes are available upon request.

Tissues were grouped into categories of relative Magmas mRNA expression according to the level of standard deviation from the mean volume (Table 1). The highest mRNA levels were present in the heart and skeletal muscle. Intermediate levels of mRNA were found in the adrenal gland, the caudate nucleus and putamen region of the brain, the pituitary gland and the testes. Somewhat surprisingly, the mRNA levels in the spleen (5664), bone marrow (5983) and peripheral blood leukocytes (5775) were all near the mean value for all tissues. mRNA expression in fetal tissues such as heart (3739) and liver (5070) were at least 3 fold lower than those of the corresponding adult tissues (shown in Table 1) demonstrating that increased transcript levels are not a marker for cellular proliferation. There was no signal in the yeast mRNA. Normalization of the tissue volumes to a membrane hybridized with an ubiquitin probe reduces the values of the cardiac tissues and skeletal muscle relative to the other tissues (data not shown), but they still remained in the high expression category.

TABLE 1

Human tissues with high expression of Magmas mRNA.

| Tissue | volume | Tissue | volume |
|---|---|---|---|
| >Two standard deviations from the mean | | | |
| right ventricle | 28329 | interventricular | 23098 |
| apex of heart | 26453 | septum | |
| skeletal muscle | 23393 | left ventricle | 20355 |
| >One standard deviation from the mean | | | |
| pituitary | 18043 | ileum | 14003 |
| left atrium | 15512 | caudate nucleus | 13968 |
| liver | 15445 | putamen | 13578 |
| heart | 14988 | right atrium | 13531 |
| adrenal gland | 14052 | testes | 13304 |

Signal volume quantified by phosphoimager. Mean volume=6644. Standard deviation (n−1)=6377. Representative of two experiments performed on the same membrane.

Figure 5A:
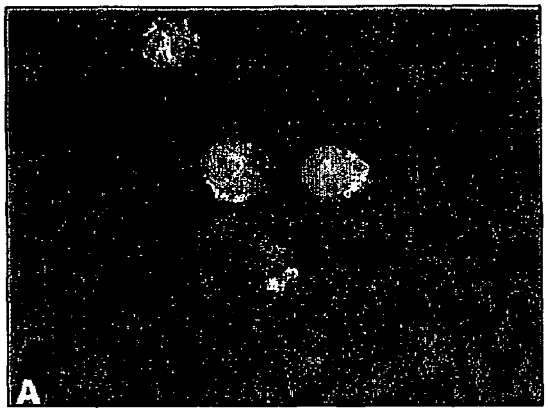
FIGS. 5A-F show the intracellular localization of Magmas. Fluorescence micrograph of PGMD1 cells incubated with rabbit anti-Magmas antibody (FIG. 5A) or preimmune antibody (FIG. 5B) followed by FITC conjugated goat anti-rabbit antibody. The nuclei are stained red by propidium iodide. PGMD1 cells transfected with a vector containing Magmas-GFP fusion protein (FIG. 5C) or vector containing GFP (FIG. 5D). Fluorescence micrograph of mitrochondrial preparations from Magmas-GFP transfected cells (FIG. 5E) or GFP transfected cells (FIG. 5F). Representative of three experiments.
Figure 5B:
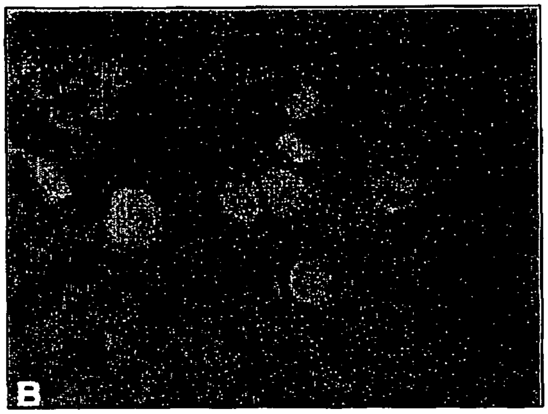

Magmas localizes to the mitochondria. Immunohistochemical staining of PGMD1 cells was used to confirm the expected mitochondria location of Magmas predicted from the amino acid composition of its leader sequence. In FIGS. 5A and 5B, cells were incubated with anti-magmas antibody (FIG. 5A) or preimmune antibody (FIG. 5B), followed by fluorescein labelled goat anti-rabbit antibody. To visualize the nuclei the cells were counterstained red with propidium iodide. FIG. 5A shows the fluorescent pattern of anti-Magmas antibody to be distributed in a punctate pattern in the cytoplasm. None of the fluorescence signal is found in the nucleus. This pattern is consistent with Magmas having mitochondrial location. PDGM1 cells similarly treated with control antibody (FIG. 5B) did not have any detectable fluorescein signal.

Figure 5C:
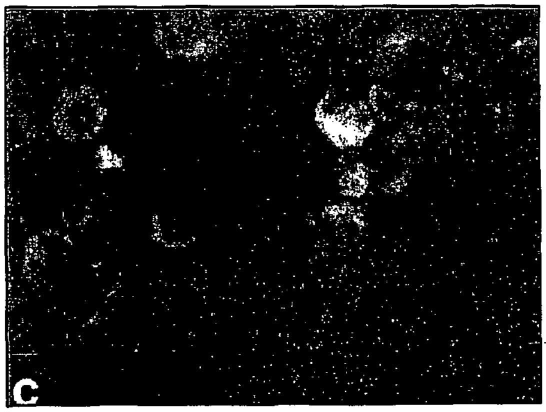
Figure 5D:
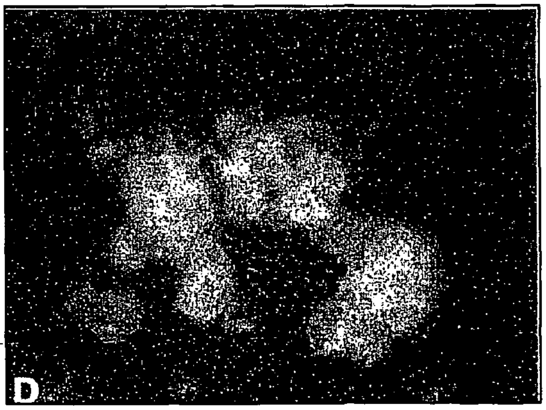
Figure 5E:
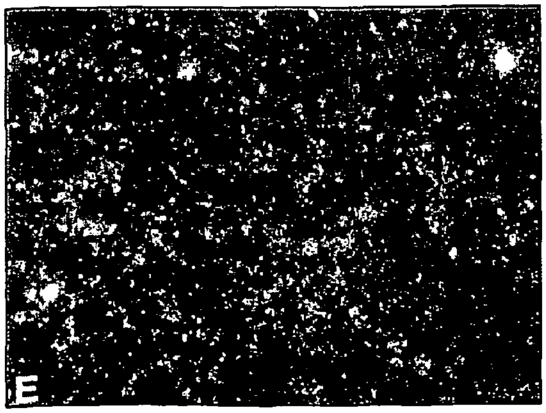
Figure 5F:

To further demonstrate the cellular location of Magmas, its cDNA was linked at the 3' end to DNA encoding GFP, and transfected into PGMD1 cells. A vector containing GFP alone was used as control. FIG. 5C shows the fluorescent signal in the cells containing Magmas-GFP in a punctate cytoplasmic distribution, identical to that observed in FIG. 5A. Control cells expressing GFP had a fluorescence signal uniformly distributed throughout the cell (FIG. 5D). Examination of mitochondrial preparations by fluorescent microscopy showed that the samples derived from cells transfected with Magmas-GFP were intensely stained (panel E), while mitochondrial preparations from the cells transfected with GFP alone had little signal (panel F).

Figure 6:
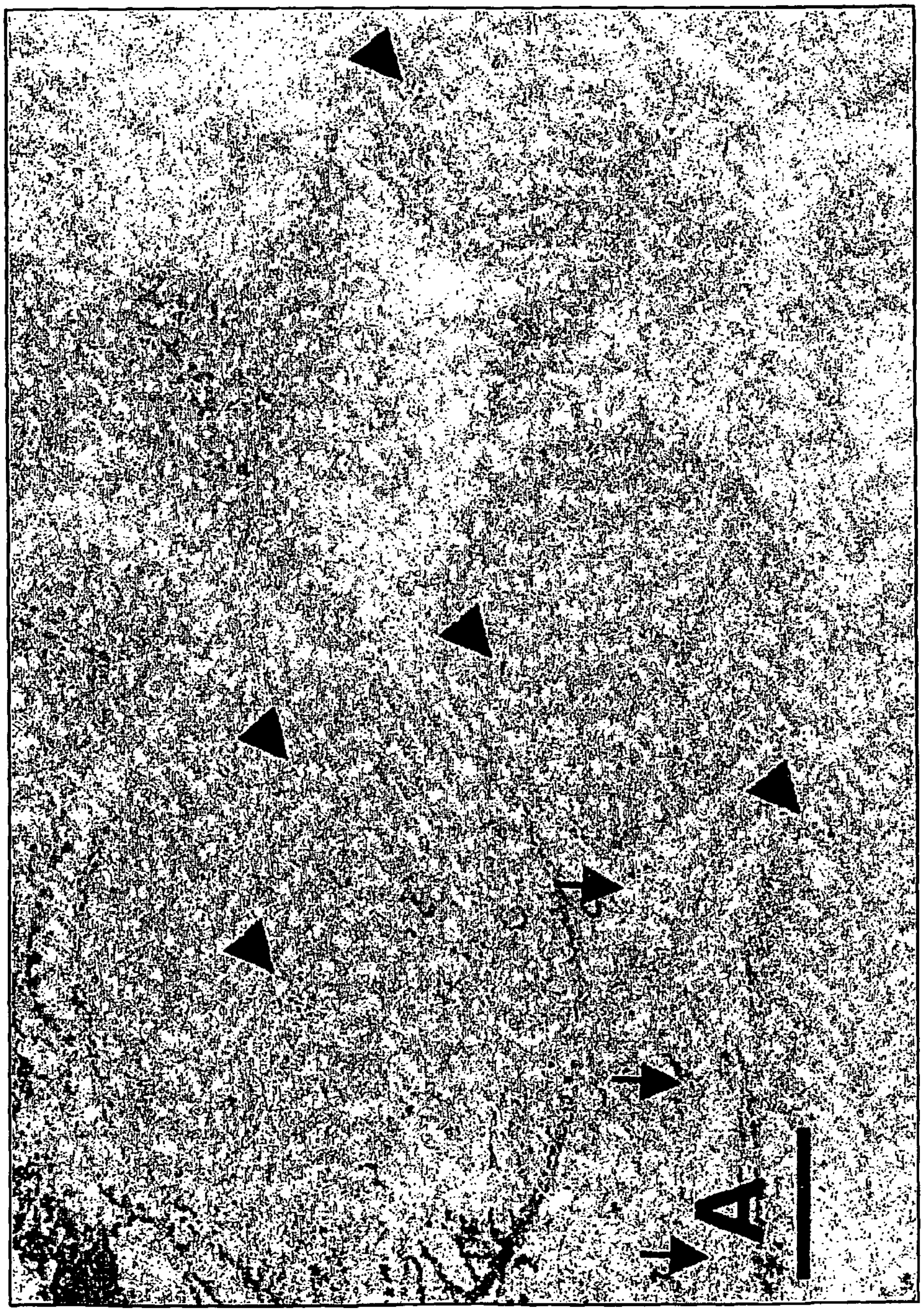
FIG. 6 demonstrates that antibody to Magmas specifically recognizes a mitochondrial protein in prostate carcinoma by electron microscopy. The arrowheads show the mitochondrial location of Magmas, while the arrows show its site of synthesis on the ribosomes.

Electron microscopy (EM) studies were then performed to verify the subcellular fractionation experiment showing that Magmas is found in the mitochondrial compartment. Tissue sections of human prostate were incubated with Magmas antibody or control antibody, followed by biotinylated goat anti-rabbit Ig and streptavidin:gold colloid. Representative electron micrographs of the results are shown in FIG. 6. In samples incubated with the anti-Magmas antibody (panel A), many clusters of electron dense gold particles are found in the mitochondria (arrowheads) and in the rough endoplasmic reticulum/ribosomal compartment (arrows). No particles are observed elsewhere in the micrograph shown. In contrast few gold grains are observed in prostate samples incubated with the control antibody (panel B). The arrow indicates the position of two grains located near the ribosomal compartment.

Greater than 100 of these electron micrographs were used to accurately quantify the distribution of gold grains per unit area In the samples stained with anti-Magmas antibody, gold particles were found to localize to the mitochondria compartment (85.93±47.51; mean particles±standard deviation per micron$^2$) or the rough endoplasmic reticulum/ribosome compartment (80.94±52.46) in comparison to the "other" compartment (14.57±8.21). The labeling of the mitochondria and ribosomal compartments were not significantly different ($p>0.05$) from each other, but each were statistically greater than the "other" compartment ($p<0.001$). A similar evaluation of the micrographs of samples incubated with control antibody showed there were 3.11±3.82 mean±SD particles/micron2 in the mitochondria, 3.22±3.27 particles/micron$^2$ in the endoplasmic reticulum/ribosome compartment and 15.89±12.29 particles/micron$^2$ in the "other" compartment Unlike the results with the anti-Magmas antibody, chi square analysis shows that the gold grains in the antibody control are randomly distributed ($p=0.15$) throughout the cell.

These EM experiments show that Magmas is found only in the mitochondria or in the closely associated ribosomal compartment where translation occurs. Thus it is likely that the upper band of the doublet in FIG. 4, lane 7 represents ribosomal associated Magmas containing its leader sequence, and the lower band the processed mature form of Magmas found in the mitochondria.

Figure 7A:
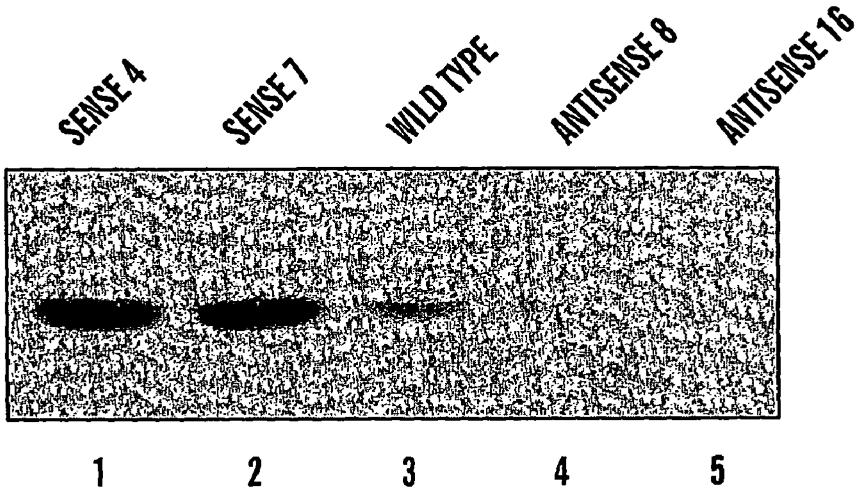
FIGS. 7A and B show the effect of Magmas expression on growth factor induced proliferation of PGMD1 cells.

Effect of Magmas expression on IL-3 and GM-CSF stimulated proliferation. Full length sense and antisense cDNA constructs of Magmas were ligated into the pREP4 vector under the control of a constitutively active CMV promotor and electroporated into PGMD1 cells. Cells were plated in microwell dishes and selected with hygromycin. The Magmas protein levels of the resulting transfectants were then determined by Western blot (FIG. 7A). Transfected cells with increased levels of Magmas are shown in lanes 1 and 2. Intermediate Magmas expression was observed in the wild type, untransfected cells (lane 3), and lanes 4 and 5 were transfected cells exhibiting reduced expression. We were not able to find any antisense transfectants that had undetectable Magmas expression.

Figure 7B:
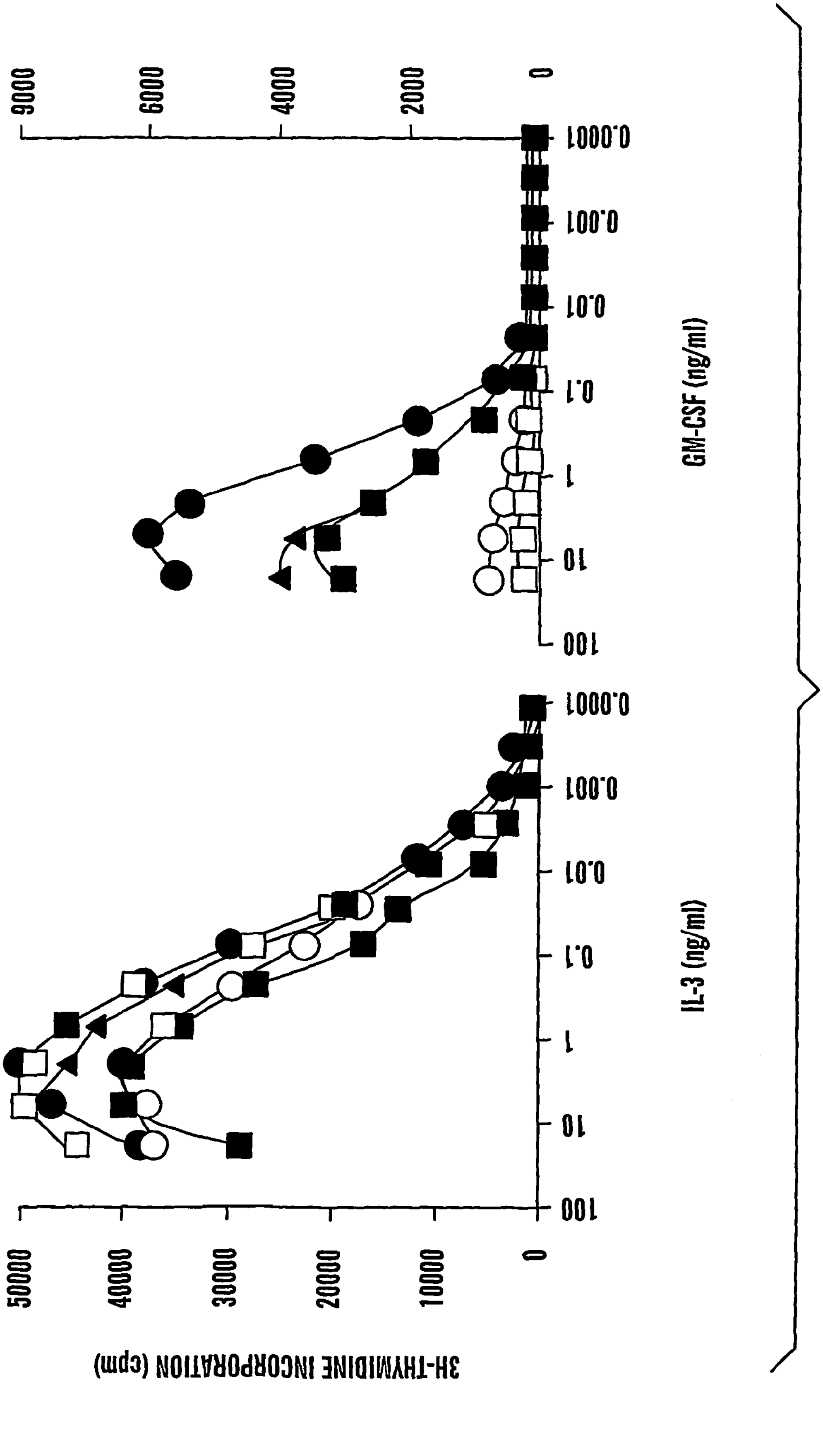
FIG. 7B shows $^3$H thymidine incorporation of wild type PGMD1 or cells transfected with sense or antisense Magmas cDNA (corresponding to FIG. 6A) cultured in various concentrations of IL-3 (left panel) or GM-CSF (right panel). Wild type (-▲-); sense 4 (-■); sense 7 (-●-□); antisense 8 (-□□-□-); antisense 16 (-□○-). Representative of two experiments.

The transfected and wild type cells from FIG. 6A were then tested for their ability to proliferate in IL-3 and GM-CSF as measured by $^3$H-thymidine incorporation. The cells with increased or reduced Magmas expression grew similarly to the wild type, non-transfected cells in the presence of IL-3 (FIG. 7B, left panel). When cultured in GM-CSF, cells with increased expression also proliferated like the wild type cells (FIG. 6B, right panel). In contrast, GM-CSF dependent proliferation was significantly impaired in cells with low levels of Magmas protein. Examination of these cells showed that reduced viability was responsible for some of the decrease in $^{3}$H-thymidine incorporation.

Magmas message levels are elevated in prostate cancer. A blot containing matched samples of cDNA derived from normal and malignant prostate tissue obtained from the same patient was probed with an $^{32}$P labelled oliginucleotide to Magmas cDNA. The results show that, the level of Magmas message is 3.5 times higher in the tumor than in normal prostate tissue for 3 cases. Even though the sample loading was normalized to 3 housekeeping genes by the manufacturer, the blot was stripped and re-probed for GAPDH expression (FIG. 7B) as an independent control for the reverse transcriptase reaction and sample loading.

Increased expression of Magmas and GM-CSF receptor in prostate tumors. Prostate samples obtained from surgical specimens were examined for Magmas expression by immunohistochemistry. High grade prostate cancer was stained with Hematoxylin -Eosin, anti-Magmas antibody and anti-GM-CSF receptor antibody. Malignant areas of the prostate sample showed significant staining with both Magmas and the GM-CSF receptor, while little staining was observed in the normal areas.

Magmas protein expression correlates to grade. Prostate samples from 13 patients were stained with an antibody against Magmas. The set included the full extent of prostate specimens from normal and benign hyperplasia to high grade metastatic prostate cancer. Normal prostate was essentially negative for Magmas expression. Benign hyperplasia was observed to have slightly elevated expression. For each carcinoma sample, the intensity of the staining was directly proportional to the grade of severity, the most severe high grade metastatic prostate cancer sample having the most intensive staining.

Magmas expression in prostate cancer is independent of the mitochondrial content of the cell. We have shown that Magmas message and protein have been shown to be higher in prostate cancer than in normal prostate tissue. This increase may result from higher Magmas expression in each mitochondria or more mitochondria cell. To accurately distinguish between these two possibilities, electron microscopy was used to quantitate the volume of mitochondria/cell and the relative expression of Magmas/mitochondria based on immunohistochemical staining. The number of mitochondria per cell in high grade prostate cancer and normal prostate tissue was not found to be statistically different. In contrast, the amount of Magmas expression in the mitochondria compartment (86 grains per micron$^{2}$ of mitochondria) was much higher than that found in the mitochondria of the normal prostate tissue, 9 grains per micron$^{2}$ of mitochondria.

Tissue dot blot and immunohistochemistry on murine embryos from E 6.5 through adult tissues. In order to gain insight about the role of Magmas in vivo, mRNA levels and protein expression were examined in murine embryos and adult tissues. A survey of Magmas mRNA in various murine tissues was performed using a tissue dot blot. The samples on the blot were normalized to eight housekeeping genes by the manufacturer. The autoradiograph of the hybridization of $^{32}$P labeled Magmas probe detected Magmas mRNA in all of the adult murine tissues as well as in the 4 whole embryo samples represented on the blot. The mean signal intensity for all adult tissue was 167,415 with a standard deviation (SD; σn-1) of 183,319. Higher levels of Magmas mRNA were found in testes (937,420; >3 SD from mean) and heart (491,236; >1SD from the mean). Liver (119,275), smooth muscle (107342) and pancreas (95,588) had the lowest signals, but they did not vary from the mean by more than 1 SD. The values from whole mouse embryos showed increasing signal intensity with age from day 11 to day 17, but the highest value was on day 7 embryo sample. The signals observed for the negative controls (yeast total RNA, yeast tRNA, *E coli* rRNA, *E coli* DNA, poly r(A), and repetitive DNA sequences) were all similar to the background. In a separate Northern blot analysis, the amount of Magmas message in placenta was similar to that of kidney.

High level of protein and mRNA levels in testes suggests that abnormal Magmas could be involved in fertility problems.

Expression of Magmas protein during murine development. Protein expression during murine development was examined at day 6.5, 10, 12.5, 14.5, 15.5 and day 18 by immunohistochernistry using anti-Magmas antibody. The amount of protein expressed was reflected by the intensity of brown precipitate resulting from the peroxidase reaction.

An intermediate amount of staining was observed in the proximal and distal endoderm including Reichert's membrane, ectoplacental cone, the embryonic ectoderm, and the decidua in the sections from a day 6.5 embryo. The section through placenta showed strong staining in the yolk sac epithelial lining, as well as the parietal endoderm and surrounding decidual cells.

In the day 12.5 embryonic heart strong staining occured in the myocytes in the atria as well as the muscle cells in the region of the atrioventricular canal. No significant staining was observed in the stromal cells of the endocardial cushions. Enhanced staining was observed in a section through a spinal cord region of the day 12.5 embryo in the notochord, the spinal ganglia and the somites, which give rise to the skin and skeletal elements.

In the day 14.5 embryo intense staining was observed in the epithelial lining of the choroid plexus of the developing brain. The primitive neuroectodermal layer also showed weaker staining. The stroma underlying the epithelial cells in the choroid plexus were negative. There was no significant staining observed in this region of the brain at day 12.5. There is strong staining in the neural cells throughout the ganglia in the section through the cervical ganglion at day 14.5. In contrast, the connective tissue surrounding the ganglia showed no significant staining. Also, in the day 14.5 embryo, strong staining was observed in the developing muscle layers. In addition, Magmas expression was also seen in the cartilage of the developing ribs as well as in the adjacent spinal ganglia adjacent to the muscle layers. The spinal ganglion cells stained less than the cervical, because they are developmentally more immature. There was strong staining in the epithelial lining of the intestinal tract as well as weaker staining in the developing muscular wall of the intestinal tract in a section through the developing intestinal tract of the day 14.5 embryo. No significant staining was observed in the developing diaphragm, however the liver was strongly positive.

In the day 18 embryo, besides the staining of the tissues already discussed there was very strong staining in the salivary gland epithelium although the surrounding connective tissue was negative. The nasal mucosal epithelium in the underlying submucosal glands, which were morphologically identifiable at day 17, also showed strong expression during this stage of development. Magmas staining for many of the other tissues at Day 18 were similar to that observed at earlier stages. The most striking exceptions occurred in skeletal and cardiac muscle, liver and bronchioles, where staining was reduced to negligible levels.

As shown in Table 2, the level of Magmas expression varied considerably during embryonic development. For example, Magmas expression was elevated in skeletal muscle, beginning at the inception of morphologically identifiable fibrils. The high level continues until sometime between day 15 and day 18 when Magmas is barely detectible. Liver, cardiac muscle, and bronchioles also had decreased Magmas expression in the day 18 sections. In contrast, staining of renal structures occurred relatively late (weak on day 15.5) and was highest on day 18.

Magmas protein expression in adult tissues Tissues from the adult mouse including brain, spinal cord, liver, spleen, pancreas, small bowel, heart, lung, kidney, ovary, uterus, and testes were evaluated for the expression of Magmas by immunohistochemistry. The amount of expression in adult tissues was reflective of the continuously high levels of Magmas protein observed throughout muscle development beginning with the first appearance of immature muscle in the embryonic tissue. Cardiac muscle fibers showed a variable reaction pattern with many strongly positive fibers in contrast to clusters of numerous negative fibers adjacent to the positive fibers. Also, even in the positive staining fibers there was variability within the fiber of the staining intensity, with some fibers showing more intense staining at the periphery of the cell or occasionally in a perinuclear distribution. Skeletal muscle fibers also showed strong positive staining. Most of the muscle cells were strongly positive, and in the skeletal muscle fibers the staining was associated with the filaments and z-bands. Cardiac muscle showed compartmentalization of the staining pattern in a coarse, granular pattern, usually with a perinuclear distribution.

Other organs, such as the kidney, pancreas, and intestine, showed positive staining for Magmas. Liver showed diffuse cytoplasmic staining in most of hepatocytes and no significant staining of the bile duct epithelium. The kidney section showed intense staining in the perirenal fat cells. Prominent expression was also observed in the proximal tubules in the renal cortex. In contrast to the cortex, the renal medulla showed little evidence of staining of the tubular epithelial cells. The glomeruli were also negative. The pancreas had diffuse positive cytoplasmic staining in the acinar cells. The intestinal tract showed positive staining in the mucosa epithelial lining of the small bowel.

The reproductive tract showed extensive evidence of Magmas expression. In the mouse, the testes were among the tissues having high levels of Magmas mRNA by Northern blot. Using antibody on adult testes strong staining in the interstitial Leydig cells as well as positive staining in the spermatocytes and spermatids was demonstrated. The epithelium lining the epididymis was also strongly positive. In the female reproductive organs, the ovary, unlike the testes, did not show much Magmas expression. Both the follicle and the perifollicular cells stained negative. The only cell populations in the ovarian tissue that were positive were the fibrous tissue and blood vessels in the ovarian stroma. The endometrial mucosal cells lining the of murine uterus sampe were weakly positive.

The brain shows strong Magmas antibody staining in the Purkinje cells of the cerebellum. The granular cells in the white matter of the cerebellar cortex do not express significant amounts of Magmas. In the cerebral cortex of the adult murine brain, high levels of Magmas expression was observed in neuronal cells, although the glial cells were generally negative or showed weak staining (data not shown). In contrast to the developing spinal cord, the adult spinal cord did not show significant staining. Minimal expression of Magmas was observed in other organs such as the lung, spleen and thymus.

As one example of a negative control for the anti-Magmas antibody was the section containing choroid plexus incubated with preimmune serum as the primary reagent. Each the panel had a matching negative control, which showed minimal to no background staining. Inclusion of a 10 fold molar excess of uncoupled immunizing peptide with the anti-Magmas antibody eliminates Magmas staining on testes and prostate sections further demonstrating the specificity of the antibody.

Discussion

Magmas protein was detected as early as the day 6.5 embryo and was found in each of the three germ lineages. Throughout development, expression was cell type specific and temporally regulated (Table 2 see below). Elevated Magmas levels were found in cells and structures such as myocytes, small bowel epithelium, kidney proximal tubules, nasal mucosa and salivary gland during embryogenesis.

In adult tissues, Magmas expression was also high in the epithelial cells as well as muscle. Epithelial cells are involved in protein and electrolyte transport and have high metabolic requirements. Magmas expression in these cells appears to correlate with function.

This relationship is illustrated by the staining pattern of the developing renal structures and the choroid plexus. In the day 14.5 embryo, there is no staining of the mesonephros, which contains primative glomeruli and collecting tubules. Weak Magmas expression becomes apparent (day 15.5) with the formation of increasing numbers of proximal and distal tubules and the initiation of urine production. Intense staining of the kidney is seen on day 18, when the organ is fully functional. In the choroid plexus, the detection of Magmas at day 14.5 correlates with the production of cerebral spinal fluid by this structure [Catala, 1998 #113][Dziegielewska, 2001 #112]. Many of the epithelial cells mentioned are affected by diabetes.

Immunohistochemistry was done on sections of brain from patients with Alzheimer's Disease (AD) and we found surprisingly, that there is reduced Magmas in the pyramidal neurons of the hippocampus. These are the cells known to be abnormal in the AD patients.

Besides ANT3, we have identified several other mitochondrial proteins that associate with Magmas.

In addition, upon screening for mutations in the different patient materials, we identified a Magmas point mutation in a patient with a mitochondrial myopathy. This patient also has an unusual mitochondrial defect because the activity of a mitochondrial enzyme, ATP synthetase, was elevated rather than reduced. ATP synthetase is one of the proteins found to associate with Magmas.

In addition, Magmas appears to interact with 3 ribosomal proteins, particularly ribosomal subunit S19, suggesting a potential role in translation.

We have also identified mutations in the blasts of the diagnostic bone marrow aspirations from patients with leukemia. All analysis done on samples obtained before therapeutic interventions on primary diagnostic bone marrow sample. In 38 AML samples, 3 deletions and 4 insertions were identified. In 68 ALL samples, one deletion and two insertions in Magmas were identified. In 66 other tumor samples and 52 normal samples, no abnormalities could be identified.

Mutations Identified AML Samples: MAKYLAQIIVMGVQVVGRAFARALRQE-FAASRFQPLRPQPPGGTAD SQRVQAEPZ (SEQ ID NO: 6), deletion of 14 codons results in 54 amino acid protein; and MAKYLAQIIVMGVQVVGRAFARALRQE-FAASRRHSRFSTCPSZ (SEQ ID NO: 7), frameshift deletion of 22 codons results in 44 amino acid protein.

Mutation Identified in Four AML and Two ALL Samples: MAKYLAQIIVMGVQVVGRAFARALRQEFAASTPZ (SEQ ID NO: 8), a 174 bp insert results in truncated 32 amino acid protein instead of 125 aa protein; and Mutation Identified in an ALL Sample: MAKYLAQIIVMGVQVVGRAFARALRQE-FAASRAEADARGRAGHRSAAASN LSGLSLQEAQQKNYEHLFKVNDKSVGGS-FYLQTKVVRAKERLDEELKIQAQ EDRKKGQMPHTZ (SEQ ID NO 9), a deletion of 13 amino acids, numbers 62-74 results in 112 amino acid protein.

Magmas sequence analysis of individuals with mitochondrial defects revealed a patient with a glutamate->glycine mutation at amino acid 72 od SEQ ID NO: 4. The mutation was present in one allele only. This patient has increased complex V activity. Clinically the patient has an encephalomyopathy.

TABLE 2

Magmas expression during murine embryogenesis.

| Tissue | 6.5 d | 10.0 d | 12.5 d | 14.5 d | 15.5 d | 18 d |
|---|---|---|---|---|---|---|
| Trophoblast | + | + | + | ND | ND | ND |
| Decidual cells | + | + | + | ND | ND | ND |
| Yolk sac | | + | + | ND | ND | ND |
| Embryonic ectoderm | + | + | + | + | weak | weak |
| Embryonic Endoderm | + | | | | | |
| Somites | | ND | + | | | |
| Cardiac muscle | | weak | + | weak | ND | − |
| Skeletal muscle | | | + | + | + | − |
| Spinal cord | | weak | + | weak | ND | ND |
| Spinal ganglia | | weak | + | + | ND | weak |
| Neural tube/Brain | | weak | + | weak | weak | weak |
| Choroid plexus | | | ND | weak | weak | weak |
| Intestine | | weak | + | + | weak | weak |
| Bronchials | | | + | + | weak | − |
| Liver | | weak | + | + | + | − |
| Salivary gland | | | | | ND | + |
| Nasal mucosa | | | | − | weak | + |
| Kidney | | | ND | − | weak | + |
| Adrenal medulla | | | | | ND | + |

REFERENCES

1. Arai K I, Lee F, Miyajima A, Miyatake S, Arai N, Yokota T (1990) Cytokines: coordinators of immune and inflammatory responses. Annu Rev Biochem 59:783.
2. Quelle F W, Sato N, Witthuhn B A, Inhom R C, Eder M, Miyajima A, Griffin J D, Ihle J N (1994) JAK2 associates with the beta c chain of the receptor for granulocyte-macrophage colony-stimulating factor, and its activation requires the membrane-proximal region. Mol Cell Biol 14:4335.
3. Chin H, Nakamura N, Kamiyama R, Miyasaka N, Ihle J N, Miura O (1996) Physical and functional interactions between Stat5 and the tyrosine-phosphorylated receptors for erythropoietin and interleukin-3. Blood 88:4415.
4. Lanfrancone L, Pelicci G, Brizzi M F, Aronica M G, Casciari C, Giuli S, Pegoraro L, Pawson T, Pelicci P G, Arouica M G (1995) Overexpression of Shc proteins potentiates the proliferative response to the granulocyte-macrophage colony-stimulating factor and recruitment of Grb2/SoS and Grb2/p140 complexes to the beta receptor subunit Oncogene 10:907.
5. Bone H, Dechert U, Jirik F, Schrader J W, Welham M J (1997) SHP1 and SHP2 protein-tyrosine phosphatases associate with betac after interleukin-3-induced receptor tyrosine phosphorylation. Identification of potential binding sites and substrates. J Biol Chem 272:14470.
6. Mui A L, Wakao H, O'Farrell A M, Harada N, Miyajima A (1995) Interleulin-3, granulocyte-macrophage colony stimulating factor and interleukin-5 transduce signals through two STAT5 homologs. Embo J 14:1166.
7. Darnell J E (1997) STATs and gene regulation. Science 277:1630.
8. Rozakis-Adcock M, Fernley R, Wade J, Pawson T, Bowtell D (1993) The SH2 and SH3 domains of mammalian Grb2 couple the EGF receptor to the Ras activator mSos1. Nature 363:83.
9. Itoh T, Muto A, Watanabe S, Miyajima A, Yokota T, Arai K (1996) Granulocyte-macrophage colony-stimulating factor provokes RAS activation and transcription of c-fos through different modes of signaling. J Biol Chem 271:7587.
10. Corey S, Eguinoa A, Puyana-Theall K, Bolen J B, Cantley L, Mollinedo F, Jackson T R, Hawkins P T, Stephens L R (1993) Granulocyte macrophage-colony stimulating factor stimulates both association and activation of phosphoinositide 3OH-kinase and src-related tyrosine kinase(s) in human myeloid derived cells. Embo J 12:2681.
11. Sato N, Sakamaki K, Terada N, Arai K, Miyajima A (1993) Signal transduction by the high-affinity GM-CSF receptor: two distinct cytoplasmic regions of the common beta subunit responsible for different signaling. Embo J 12:4181.
12. Li Y, Shen B F, Karanes C, Sensenbrenner L, Chen B (1995) Association between Lyn protein tyrosine kinase (p53/561yn) and the beta subunit of the granulocyte-macrophage colony-stimulating factor (GM-CSF) receptors in a GM-CSF-dependent human megakaryocytic leukemia cell line (M-07e). J Immunol 155:2165.
13. Torigoe T, O'Connor R, Santoli D, Reed J C (1992) Interleukin-3 regulates the activity of the LYN protein-tyrosine kinase in myeloid-committed leukemic cell lines. Blood 80:617.
14. Welham M J, Dechert U, Leslie K B, Jirik F, Schrader J W (1994) Interleukin (IL)-3 and granulocyte/macrophage colony-stimulating factor, but not IL-4, induce tyrosine phosphorylation, activation, and association of SHPTP2 with Grb2 and phosphatidylinositol 3'-kinase. J Biol Chem 269:23764.
15. Geij sen N, Spaargaren M, Raaijmakers J A, Lammers J W, Koenderman L, Coffer P J (1999) Association of RACK1 and PKCbeta with the common beta-chain of the IL-5/IL-3/GM-CSF receptor. Oncogene 18:5126.
16. Okuda K, Smith L, Griffin J D, Foster R (1997) Signaling functions of the tyrosine residues in the betac chain of the granulocyte-macrophage colony-stimulating factor receptor. Blood 90:4759.

17. Itoh T, Liu R, Yokota T, Arai K I, Watanabe S (1998) Definition of the role of tyrosine residues of the common beta subunit regulating multiple signaling pathways of granulocyte-macrophage colony-stimulating factor receptor. Mol Cell Biol 18:742.

18. Orban P C, Levings M K, Schrader J W (1999) Heterodimerization of the alpha and beta chains of the interleukin-3 (IL-3) receptor is necessary and sufficient for IL-3-induced mitogenesis. Blood 94:1614.

19. Matsuguchi T, Zhao Y, Lilly M B, Kraft A S (1997) The cytoplasmic domain of granulocyte-macrophage colony-stimulating factor (GM-CSF) receptor alpha subunit is essential for both GM-CSF-mediated growth and differentiation. J Biol Chem 272:17450.

20. Weiss M, Yokoyama C, Shikama Y, Naugle C, Druker B, Sieff C A (1993) Human granulocyte-macrophage colony-stimulating factor receptor signal transduction requires the proximal cytoplasmic domains of the alpha and beta subunits. Blood 82:3298.

21. Ronco L V, Doyle S E, Raines M, Park L S, Gasson J C (1995) Conserved amino acids in the human granulocyte-macrophage colony-stimulating factor receptor-binding subunit essential for tyrosine phosphorylation and proliferation. J Immunol 154:3444.

22. Barry S C, Korpelainen E, Sun Q, Stomski F C, Moretti P A, Wakao H, D'Andrea R J, Vadas M A, Lopez A F, Goodall G J (1997) Roles of the N and C terminal domains of the interleukin-3 receptor alpha chain in receptor function. Blood 89:842.

23. Hawley R G, Fong A Z, Ngan B Y, de Lanux V M, Clark S C, Hawley T S (1993) Progenitor cell hyperplasia with rare development of myeloid leukemia in interleukin 11 bone marrow chimeras. J Exp Med 178:1175.

24. Sambrook J, Fritsch E F, Maniatis T. 1990. Molecular Cloning: A Laboratory Manual. Cold Spring Harbor, NY:Cold Spring Harbor Laboratory Press, Unit 7.43-7.5.

25. Schultz J, Milpetz F, Bork P, Ponting C P (1998) SMART, a simple modular architecture research tool: identification of signaling domains. Proc Natl Acad Sci USA 95:5857.

26. Schultz J, Copley R R, Doerks T, Ponting C P, Bork P (2000) SMART: a web-based tool for the study of genetically mobile domains. Nucleic Acids Res 28:231.

27. Frohman M A, Dush M K, Martin G R (1988) Rapid production of full-length cDNAs from rare transcripts: amplification using a single gene-specific oligonucleotide primer. Proc Natl Acad Sci USA 85:8998.

28. Ohara O, Dorit R L, Gilbert W (1989) One-sided polymerase chain reaction: the amplification of cDNA. Proc Natl Acad Sci U S A 86:5673.

29. Heinemeyer T, Wingender E, Reuter I, Hermjakob H, Kel A E, Kel O V, Ignatieva E V, Ananko E A, Podkolodnaya O A, Kolpakov F A, Podkolodny N L, Kolchanov N A (1998) Databases on transcriptional regulation: TRANSFAC, TRRD and COMPEL. Nucleic Acids Res 26:362.

30. Bonifacino J S, Dasso M, Harford J B, Lippincott-Schwartz J, Yamada K M. 2000. Current Protocols in Cell Biology. K. Morgan, S., editor. John Wiley & Sons, Inc., New York, N.Y. Unit 3.3.

31. Harlow E, Lane D. 1988. Antibodies, A Laboratory Manual. Cold Spring Harbor: Cold Spring Harbor Laboratory, 479-494.

32. Coligan J E, Dunn B M, Ploegh H L, Speicher D W, Wingfield P T. 2000. Current Protocols in Protein Science. V. B. Chanda, editor. John Wiley & Sons, Inc., New York, N.Y.

33. Adunyah S E, Unlap T M, Wagner F, Kraft A S (1991) Regulation of c-jun expression and AP-1 enhancer activity by granulocyte-macrophage colony-stimulating factor. J Biol Chem 266:5670.

34. Hromas R, Collins S J, Hickstein D, Raskind W, Deaven L L, O'Hara P, Hagen F S, Kaushansky K (1991) A retinoic acid-responsive human zinc finger gene, MZF-1, preferentially expressed in myeloid cells. J Biol Chem 266:14183.

35. Bavisotto L, Kaushansky K, Lin N, Hromas R (1991) Antisense oligonucleotides from the stage-specific myeloid zinc finger gene MZF-1 inhibit granulopoiesis in vitro. J Exp Med 174:1097.

36. Lithgow T (2000) Targeting of proteins to mitochondria. FEBS Lett 476:22.

37. Pfanner N (2000) Protein Sorting: Recognizing mitochondrial presequences. Current Biology 10:R412.

38. Alberts B, Bray D, Lewis J, Raff M, Roberts K, Watson J D. 1994. Molecular Biology of the Cell. New York:Garland Publishing, Inc., Pages.

39. Schatz G, Dobberstein B (1996) Common principles of protein translocation across membranes. Science 271:1519.

40. Senis Y, Zirngibl R, McVeigh J, Haman A, Hoang T, Greer P A (1999) Targeted disruption of the murine fps/fes proto-oncogene reveals that Fps/Fes kinase activity is dispensable for hematopoiesis. Mol Cell Biol 19:7436.

41. Chao J R, Wang J M, Lee S F, Peng H W, Lin Y H, Chou C H, Li J C, Huang H M, Chou C K, Kuo M L, Yen J J, Yang-Yen H F (1998) mcl-1 is an immediate-early gene activated by the granulocyte-macrophage colony-stimulating factor (GM-CSF) signaling pathway and is one component of the GM-CSF viability response. Mol Cell Biol 18:4883.

42. Krajewski S, Bodrug S, Krajewska M, Shabaik A, Gascoyne R, Berean K, Reed J C (1995) Immunohistochemical analysis of Mcl-1 protein in human tissues. Differential regulation of Mcl-1 and Bcl-2 protein production suggests a unique role for Mcl-1 in control of programmed cell death in vivo. Am J Pathol 146: 1309.

43. Yang T, Kozopas K M, Craig R W (1995) The intracellular distribution and pattern of expression of Mcl-1 overlap with, but are not identical to, those of Bcl-2. J Cell Biol 128:1173.

44. Sullivan G W, Carper H T, Mandell G L (1993) The effect of three human recombinant hematopoietic growth factors (granulocyte-macrophage colony-stimulating factor, granulocyte colony-stimulating factor, and interleukin-3) on phagocyte oxidative activity. Blood 81:1863.

45. Kapp A, Zeck-Kapp G (1990) Activation of the oxidative metabolism in human polymorphonuclear neutrophilic granulocytes: the role of immuno-modulating cytokines. J Invest Dermatol 95:94S.

46. Nathan C F (1989) Respiratory burst in adherent human neutrophils: triggering by colony-stimulating factors CSF-GM and CSF-G. Blood 73:301.

47. Ahmed N, Kansara M, Berridge M V (1997) Acute regulation of glucose transport in a monocyte-macrophage cell line: Glut-3 affinity for glucose is enhanced during the respiratory burst. Biochem J 327: 369.

48. Khwaja A, Addison I E, Johnson B, Yong K, Linch D C (1994) Interleukin-3 administration enhances human monocyte function in vivo. Br J Haematol 88:515.
49. Coleman D L, Chodakewitz J A, Bartiss A H, Mellors J W (1988) Granulocyte-macrophage colony-stimulating factor enhances selective effector functions of tissue-derived macrophages. Blood 72:573.
50. Suchard S J, Boxer L A (1994) Exocytosis of a subpopulation of specific granules coincides with H202 production in adherent human neutrophils. J Immunol 152:290.
51. Spolarics Z, Schuler A, Bagby G J, Lang C H, Nelson S, Spitzer J J (1992) In vivo metabolic response of hepatic nonparenchymal cells and leukocytes to granulocyte-macrophage colony-stimulating factor. J Leukoc Biol 51:360.
52. Hamilton J A, Vairo G, Lingelbach S R (1988) Activation and proliferation signals in murine macrophages: stimulation of glucose uptake by hemopoietic growth factors and other agents. J Cell Physiol 134:405.
53. Spielholz C, Heaney M L, Morrison M E, Houghton A N, Vera J C, Golde D W (1995) Granulocyte-macrophage colony-stimulating factor signals for increased glucose uptake in human melanoma cells. Blood 85:973.
54. Wada H G, Indelicato S R, Meyer L, Kitamura T, Miyajima A, Kirk G, Muir V C, Parce J W (1993) GM-CSF triggers a rapid, glucose dependent extracellular acidification by TF-1 cells: evidence for sodium/proton antiporter and PKC mediated activation of acid production. J Cell Physiol 154:129.
55. Lopez A F, Williamson D J, Gamble J R, Begley C G, Harlan J M, Klebanoff S J, Waltersdorph A, Wong G, Clark S C, Vadas M A (1986) Recombinant human granulocyte-macrophage colony-stimulating factor stimulates in vitro mature human neutrophil and eosinophil function, surface receptor expression, and survival. J Clin Invest 78:1220.
56. Tu J, Karasawas N, Heaney M L, Vera J C, Golde D W (2000) Molecular characterization of a granulocyte macrophage-colony-stimulating factor receptor alpha subunit-associated protein, GRAP. Blood 96:794.
57. Fabian I, Kletter Y, Mor S, Geller-Bernstein C, Ben-Yaakov M, Volovitz B, Golde D W (1992) Activation of human eosinophil and neutrophil functions by haematopoietic growth factors: comparisons of IL-1, IL-3, IL-5 and GM-CSF. Br J Haematol 80:137.
58. Blom M, Tool A T, Kok P T, Koenderman L, Roos D, Verhoeven A J (1994) Granulocyte-macrophage colony-stimulating factor, interleukin-3 (IL-3), and IL-5 greatly enhance the interaction of human eosinophils with opsonized particles by changing the affinity of complement receptor type 3. Blood 83:2978.

All references described herein and throughout the specification are incorporated herein by reference in their entirety.

We claim:

1. A method of identifying a disease condition comprising obtaining a biological sample from an individual and analyzing the biological sample for a variation in the Magmas protein of SEQ ID NO:4, wherein said variation results in a truncation of the Magmas protein, wherein said variation indicates a disease condition, and wherein the disease condition is AML or ALL.

2. A method of identifying a disease condition comprising obtaining a biological sample from an individual and analyzing the biological sample for a variation in the Magmas protein of SEQ ID NO:4, wherein said variation indicates a disease condition, wherein the variation results in a truncation of downstream of amino acid 29 of SEQ ID NO: 4 and the disease condition is AML or ALL.

3. The method of claim 1, wherein the variation of the Magmas protein of SEQ ID NO:4 is detected using an antibody to the Magmas protein.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Probe

<400> SEQUENCE: 1

gagcgtccgc catggccaag ta                                          22


<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Human/mouse
      peptide used to generate antibodies
<220> FEATURE:
<221> NAME/KEY: MOD_RES
<222> LOCATION: (5)
<223> OTHER INFORMATION: Arg or Lys
<220> FEATURE:
<221> NAME/KEY: MOD_RES
<222> LOCATION: (17)
<223> OTHER INFORMATION: Lys or Leu
<220> FEATURE:
<221> NAME/KEY: MOD_RES
<222> LOCATION: (19)
<223> OTHER INFORMATION: Lys or His

<400> SEQUENCE: 2
```

-continued

```
Asp Glu Glu Leu Xaa Ile Gln Ala Gln Glu Asp Arg Glu Lys Gly Gln
  1               5                  10                  15

Xaa Pro Xaa Thr
             20


<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Human/mouse
      peptide used to generate antibodies
<220> FEATURE:
<221> NAME/KEY: MOD_RES
<222> LOCATION: (11)
<223> OTHER INFORMATION: Gln or Arg

<400> SEQUENCE: 3

Arg Ala Leu Arg Gln Glu Phe Ala Ala Ser Xaa Ala Ala Ala Asp Ala
  1               5                  10                  15

Arg Gly Arg Cys
             20


<210> SEQ ID NO 4
<211> LENGTH: 125
<212> TYPE: PRT
<213> ORGANISM: Homo sapiens

<400> SEQUENCE: 4

Met Ala Lys Tyr Leu Ala Gln Ile Ile Val Met Gly Val Gln Val Val
  1               5                  10                  15

Gly Arg Ala Phe Ala Arg Ala Leu Arg Gln Glu Phe Ala Ala Ser Arg
             20                  25                  30

Ala Ala Ala Asp Ala Arg Gly Arg Ala Gly His Arg Ser Ala Ala Ala
         35                  40                  45

Ser Asn Leu Ser Gly Leu Ser Leu Gln Glu Ala Gln Gln Ile Leu Asn
     50                  55                  60

Val Ser Lys Leu Ser Pro Glu Glu Val Gln Lys Asn Tyr Glu His Leu
 65                  70                  75                  80

Phe Lys Val Asn Asp Lys Ser Val Gly Gly Ser Phe Tyr Leu Gln Ser
                 85                  90                  95

Lys Val Val Arg Ala Lys Glu Arg Leu Asp Glu Glu Leu Lys Ile Gln
            100                 105                 110

Ala Gln Glu Asp Arg Glu Lys Trp Gln Met Pro His Thr
        115                 120                 125


<210> SEQ ID NO 5
<211> LENGTH: 41
<212> TYPE: PRT
<213> ORGANISM: Homo sapiens

<400> SEQUENCE: 5

Met Ala Lys Tyr Leu Ala Gln Ile Ile Val Met Gly Val Gln Val Val
  1               5                  10                  15

Gly Arg Val Phe Ala Arg Ala Leu Arg Gln Glu Phe Ala Phe Ala Arg
             20                  25                  30

Ala Leu Arg Gln Glu Phe Ala Glu Leu
         35                  40


<210> SEQ ID NO 6
<211> LENGTH: 54
```

-continued

<212> TYPE: PRT
<213> ORGANISM: Homo sapiens

<400> SEQUENCE: 6

Met Ala Lys Tyr Leu Ala Gln Ile Ile Val Met Gly Val Gln Val Val
1 5 10 15

Gly Arg Ala Phe Ala Arg Ala Leu Arg Gln Glu Phe Ala Ala Ser Arg
20 25 30

Phe Gln Pro Leu Arg Pro Gln Pro Pro Gly Gly Thr Ala Asp Ser Gln
35 40 45

Arg Val Gln Ala Glu Pro
50

<210> SEQ ID NO 7
<211> LENGTH: 42
<212> TYPE: PRT
<213> ORGANISM: Homo sapiens

<400> SEQUENCE: 7

Met Ala Lys Tyr Leu Ala Gln Ile Ile Val Met Gly Val Gln Val Val
1 5 10 15

Gly Arg Ala Phe Ala Arg Ala Leu Arg Gln Glu Phe Ala Ala Ser Arg
20 25 30

Arg His Ser Arg Phe Ser Thr Cys Pro Ser
35 40

<210> SEQ ID NO 8
<211> LENGTH: 33
<212> TYPE: PRT
<213> ORGANISM: Homo sapiens

<400> SEQUENCE: 8

Met Ala Lys Tyr Leu Ala Gln Ile Ile Val Met Gly Val Gln Val Val
1 5 10 15

Gly Arg Ala Phe Ala Arg Ala Leu Arg Gln Glu Phe Ala Ala Ser Thr
20 25 30

Pro

<210> SEQ ID NO 9
<211> LENGTH: 112
<212> TYPE: PRT
<213> ORGANISM: Homo sapiens

<400> SEQUENCE: 9

Met Ala Lys Tyr Leu Ala Gln Ile Ile Val Met Gly Val Gln Val Val
1 5 10 15

Gly Arg Ala Phe Ala Arg Ala Leu Arg Gln Glu Phe Ala Ala Ser Arg
20 25 30

Ala Glu Ala Asp Ala Arg Gly Arg Ala Gly His Arg Ser Ala Ala Ala
35 40 45

Ser Asn Leu Ser Gly Leu Ser Leu Gln Glu Ala Gln Gln Lys Asn Tyr
50 55 60

Glu His Leu Phe Lys Val Asn Asp Lys Ser Val Gly Gly Ser Phe Tyr
65 70 75 80

Leu Gln Thr Lys Val Val Arg Ala Lys Glu Arg Leu Asp Glu Glu Leu
85 90 95

Lys Ile Gln Ala Gln Glu Asp Arg Lys Lys Gly Gln Met Pro His Thr
100 105 110

-continued

<210> SEQ ID NO 10
<211> LENGTH: 125
<212> TYPE: PRT
<213> ORGANISM: Mus musculus

<400> SEQUENCE: 10

```
Met Ala Lys Tyr Leu Ala Gln Ile Ile Val Met Gly Val Gln Val Val
  1               5                  10                  15

Gly Arg Ala Phe Ala Arg Ala Leu Arg Gln Glu Phe Ala Ala Ser Gln
             20                  25                  30

Ala Ala Ala Asp Ala Arg Gly Arg Ala Gly His Gln Ser Ala Ala Ala
         35                  40                  45

Ser Asn Leu Ser Gly Leu Ser Leu Gln Glu Ala Gln Gln Ile Leu Asn
     50                  55                  60

Val Ser Lys Leu Ser Pro Glu Glu Val Gln Lys Asn Tyr Glu His Leu
 65                  70                  75                  80

Phe Lys Val Asn Asp Lys Ser Val Gly Gly Ser Phe Tyr Leu Gln Ser
                 85                  90                  95

Lys Val Val Arg Ala Lys Glu Arg Leu Asp Glu Glu Leu Arg Ile Gln
            100                 105                 110

Ala Gln Glu Asp Arg Glu Lys Gly Gln Lys Pro Lys Thr
        115                 120                 125
```

<210> SEQ ID NO 11
<211> LENGTH: 496
<212> TYPE: DNA
<213> ORGANISM: Homo sapiens

<400> SEQUENCE: 11

```
aattcggcac caggggagtt tgagccccgg agcagagcgg ctgccatggc caagtacctg      60

gcccagatca ttgtgatggg cgtgcaggtg gtgggcaggg cctttgcacg ggccttgcgg     120

caggagtttg cagccagccg ggccgcagct gatgcccgag gacgcgctgg acaccggtct     180

gcagccgctt ccaacctctc cggcctcagc ctccaggagg cacagcagat tctcaacgtg     240

tccaagctga gccctgagga ggtccagaag aactatgaac acttatttaa ggtgaatgat     300

aaatccgtgg gtggctcctt ctacctgcag tcaaaggtgg tccgcgcaaa ggagcgcctg     360

gatgaggaac tcaaaatcca ggcccaggag gacagagaaa aatggcagat gccccatacg     420

tgactgctcg gctccccccg cccaccccgc cgcctctaat ttatagcttg gtaataaatt     480

tcttttctgc aaaaaa                                                     496
```

<210> SEQ ID NO 12
<211> LENGTH: 536
<212> TYPE: DNA
<213> ORGANISM: Mus musculus
<220> FEATURE:
<221> NAME/KEY: CDS
<222> LOCATION: (79)..(453)

<400> SEQUENCE: 12

```
ctgacccacc agcaaccctt gagctggtcc cactgggtcg ggaagcggca cccgtccccc      60

taaagtggag cgtccgcc atg gcc aag tac ctg gcc cag atc att gtg atg      111
                    Met Ala Lys Tyr Leu Ala Gln Ile Ile Val Met
                      1               5                  10

ggt gtg cag gtg gtg ggc aga gcc ttt gcc agg gcc ctg agg cag gag      159
Gly Val Gln Val Val Gly Arg Ala Phe Ala Arg Ala Leu Arg Gln Glu
             15                  20                  25
```

-continued

```
ttt gca gcc agc cag gca gcc gct gac gct cga ggg cgt gct ggg cac      207
Phe Ala Ala Ser Gln Ala Ala Ala Asp Ala Arg Gly Arg Ala Gly His
        30                  35                  40

cag tct gca gct gca tcc aat ctc tct ggc ctc agc ctc cag gaa gcc      255
Gln Ser Ala Ala Ala Ser Asn Leu Ser Gly Leu Ser Leu Gln Glu Ala
    45                  50                  55

cag cag att ctc aac gtc tcc aag ctg agc ccc gag gag gtc cag aag      303
Gln Gln Ile Leu Asn Val Ser Lys Leu Ser Pro Glu Glu Val Gln Lys
 60                 65                  70                  75

aat tat gaa cac cta ttt aaa gtg aat gat aag tcc gtg ggt ggc tct      351
Asn Tyr Glu His Leu Phe Lys Val Asn Asp Lys Ser Val Gly Gly Ser
                80                  85                  90

ttc tac ctg cag tca aag gtt gtc cgt gca aag gaa cgt cta gat gag      399
Phe Tyr Leu Gln Ser Lys Val Val Arg Ala Lys Glu Arg Leu Asp Glu
            95                 100                 105

gaa ctc cga ata caa gcc cag gaa gac aga gag aaa ggg cag aag ccc      447
Glu Leu Arg Ile Gln Ala Gln Glu Asp Arg Glu Lys Gly Gln Lys Pro
        110                 115                 120

aaa acg tgactgctgg gctctccaca ccccagccat tgcctcataa tttatagcct       503
Lys Thr
    125

agtaataaat gtctttgcgt gtttcttcac tgc                                 536
```